(12) United States Patent
Reisch et al.

(10) Patent No.: US 8,642,809 B2
(45) Date of Patent: Feb. 4, 2014

(54) METHODS OF SYNTHESIS OF CERTAIN HYDROXAMIC ACID COMPOUNDS

(75) Inventors: Helge A. Reisch, Rensselaer, NY (US); Peter Leeming, Schenectady, NY (US); Prasad S. Raje, Mumbai (IN)

(73) Assignee: Topotarget UK Ltd., Oxford (GB)

( * ) Notice: Subject to any disclaimer, the term of this patent is extended or adjusted under 35 U.S.C. 154(b) by 608 days.

(21) Appl. No.: 12/678,594

(22) PCT Filed: Sep. 23, 2008

(86) PCT No.: PCT/GB2008/003226
§ 371 (c)(1),
(2), (4) Date: Jul. 2, 2010

(87) PCT Pub. No.: WO2009/040517
PCT Pub. Date: Apr. 2, 2009

(65) Prior Publication Data
US 2010/0286279 A1    Nov. 11, 2010

Related U.S. Application Data

(60) Provisional application No. 60/974,880, filed on Sep. 25, 2007.

(51) Int. Cl.
*C07C 303/00* (2006.01)
(52) U.S. Cl.
USPC .......................................................... 564/86
(58) Field of Classification Search
USPC .......................................................... 564/86
See application file for complete search history.

(56) References Cited

U.S. PATENT DOCUMENTS

| | | | |
|---|---|---|---|
| 4,642,316 A | 2/1987 | Fawzi et al. | |
| 6,071,923 A | 6/2000 | Nudelman et al. | |
| 6,342,219 B1 | 1/2002 | Thorpe et al. | |
| 6,541,661 B1 | 4/2003 | Delorme et al. | |
| 6,656,905 B1 | 12/2003 | Mori et al. | |
| 6,888,027 B2 | 5/2005 | Watkins et al. | |
| 7,183,298 B2 | 2/2007 | Watkins et al. | |
| RE39,850 E | 9/2007 | Delorme et al. | |
| 7,375,137 B2 | 5/2008 | Bacopoulos et al. | |
| 7,407,988 B2 | 8/2008 | Bacopoulos et al. | |
| 7,465,731 B2 | 12/2008 | Ishibashi et al. | |
| 7,491,748 B2 | 2/2009 | Tani et al. | |
| 7,495,022 B2 | 2/2009 | Kim et al. | |
| 7,557,140 B2 | 7/2009 | Kalvinsh et al. | |
| 2003/0170319 A1 | 9/2003 | Netke et al. | |
| 2003/0235588 A1 | 12/2003 | Richon et al. | |
| 2004/0018968 A1 | 1/2004 | Sgouros et al. | |
| 2004/0072735 A1 | 4/2004 | Richon et al. | |
| 2004/0077726 A1 | 4/2004 | Watkins et al. | |
| 2004/0092598 A1 | 5/2004 | Watkins et al. | |
| 2004/0127523 A1 | 7/2004 | Bacopoulos et al. | |
| 2004/0132825 A1 | 7/2004 | Bacopoulos et al. | |
| 2004/0198830 A1 | 10/2004 | Watkins et al. | |
| 2004/0220242 A1 | 11/2004 | Shapiro | |
| 2004/0254220 A1 | 12/2004 | Bressi et al. | |
| 2005/0085515 A1 | 4/2005 | Watkins et al. | |
| 2005/0107445 A1 | 5/2005 | Watkins et al. | |
| 2005/0119305 A1 | 6/2005 | Naka et al. | |
| 2005/0124679 A1 | 6/2005 | Kim et al. | |
| 2005/0222013 A1 | 10/2005 | Jung et al. | |
| 2005/0245439 A1 | 11/2005 | Chung | |
| 2005/0288227 A1 | 12/2005 | Marks et al. | |
| 2006/0052599 A1 | 3/2006 | Ishibashi et al. | |
| 2006/0058298 A1 | 3/2006 | Delorme et al. | |
| 2006/0160897 A1 | 7/2006 | Pelicci et al. | |
| 2006/0229237 A1 | 10/2006 | Chung et al. | |
| 2006/0270016 A1 | 11/2006 | Holm | |
| 2007/0004806 A1 | 1/2007 | Kalvinsh et al. | |
| 2007/0037738 A1 | 2/2007 | Hentsch et al. | |
| 2007/0054260 A1 | 3/2007 | Trepel et al. | |
| 2007/0060614 A1 | 3/2007 | Bacopoulos et al. | |
| 2007/0110719 A1 | 5/2007 | Holm | |
| 2007/0148228 A1 | 6/2007 | Cumming et al. | |
| 2007/0232528 A1 | 10/2007 | Franke | |
| 2007/0292512 A1 | 12/2007 | Leonard et al. | |
| 2008/0004311 A1 | 1/2008 | Hellberg | |
| 2008/0045445 A1 | 2/2008 | Chen et al. | |

(Continued)

FOREIGN PATENT DOCUMENTS

| EP | 0787742 | 8/1997 |
|---|---|---|
| EP | 1293205 | 3/2003 |
| EP | 1426054 | 6/2004 |
| JP | 10114681 | 5/1998 |
| WO | 0226696 | 4/2002 |
| WO | 0230879 | 4/2002 |
| WO | 02090534 | 11/2002 |
| WO | 03066579 | 8/2003 |
| WO | 03075929 | 9/2003 |
| WO | 03082288 | 10/2003 |

(Continued)

OTHER PUBLICATIONS

Finn et al., Helvetica Chimica Acta 2005, 88,1630-1657.*
Adler, J.T. et al., "Inhibition of Growth in Medullary Thyroid Cancer Cells with Histone Deacetylase Inhibitors and Lithium Chloride", Journal of Surgical Research, (2010), vol. 159, pp. 640-644.

(Continued)

*Primary Examiner* — Johann R Richter
*Assistant Examiner* — Kofi Adzamli
(74) *Attorney, Agent, or Firm* — Beverly W. Lubit; Greenberg Traurig, LLP

(57) ABSTRACT

The present invention pertains to the general field of chemical synthesis, and more particularly to methods for the synthesis of certain hydroxamic acid compounds, and in particular, (E)-N-hydroxy-3-(3-phenylsulfamoyl-phenyl)-acrylamide, also known as PXD101 and Belinostat®, comprising, for example, the steps of: (SAF) sulfonamide formation; ($PUR_C$) optional purification; (AAA) alkenyl-acid addition, comprising: either (i): the steps of, in order: (ACAEA) alkenyl-carboxylic acid ester addition; ($PUR_E$) optional purification; and (CAD) carboxylic acid deprotection; or (ii): the step of: (ACAA) alkenyl-carboxylic acid addition; ($PUR_F$) optional purification; (HAF) hydroxamic acid formation; and ($PUR_G$) optional purification.

20 Claims, No Drawings

(56) References Cited

U.S. PATENT DOCUMENTS

| | | | |
|---|---|---|---|
| 2008/0119424 A1 | 5/2008 | Bernards et al. | |
| 2008/0146623 A1 | 6/2008 | Deziel et al. | |
| 2008/0161401 A1 | 7/2008 | Watkins et al. | |
| 2008/0194690 A1 | 8/2008 | Bastin et al. | |
| 2008/0207724 A1 | 8/2008 | Mink et al. | |
| 2008/0213399 A1 | 9/2008 | Lichenstein et al. | |
| 2008/0214547 A1 | 9/2008 | Srivastava et al. | |
| 2008/0242648 A1 | 10/2008 | Ordentlich et al. | |
| 2008/0249137 A1 | 10/2008 | Lin et al. | |
| 2008/0249179 A1 | 10/2008 | Bacopoulos et al. | |
| 2008/0274120 A1 | 11/2008 | Lichenstein et al. | |
| 2008/0292616 A1 | 11/2008 | Bates et al. | |
| 2009/0012175 A1 | 1/2009 | Bacopoulos et al. | |
| 2009/0023149 A1 | 1/2009 | Knudsen | |
| 2009/0036435 A1 | 2/2009 | Curry et al. | |
| 2009/0048156 A1 | 2/2009 | Brodie et al. | |
| 2009/0060873 A1 | 3/2009 | Sporn et al. | |
| 2009/0098054 A1 | 4/2009 | Kufe | |
| 2009/0105168 A1 | 4/2009 | Guber et al. | |
| 2009/0142337 A1 | 6/2009 | Squires | |
| 2009/0186809 A1 | 7/2009 | Hentsch et al. | |
| 2009/0232800 A1 | 9/2009 | Holm | |
| 2009/0233902 A1 | 9/2009 | Vennemann et al. | |
| 2009/0246169 A1 | 10/2009 | Vennemann et al. | |
| 2009/0246198 A1 | 10/2009 | Dong et al. | |
| 2009/0270497 A1 | 10/2009 | Buggy | |
| 2009/0286862 A1 | 11/2009 | Narita et al. | |
| 2009/0298924 A1 | 12/2009 | Davidson et al. | |
| 2009/0311175 A1 | 12/2009 | Brose | |

FOREIGN PATENT DOCUMENTS

| | | |
|---|---|---|
| WO | 03087057 | 10/2003 |
| WO | 03092686 | 11/2003 |
| WO | 2004009536 | 1/2004 |
| WO | 2004013130 | 2/2004 |
| WO | 2004043962 | 5/2004 |
| WO | 2004063146 | 7/2004 |
| WO | 2004063169 | 7/2004 |
| WO | 2004064727 | 8/2004 |
| WO | 2004069803 | 8/2004 |
| WO | 2004069823 | 8/2004 |
| WO | 2004071400 | 8/2004 |
| WO | 2004072047 | 8/2004 |
| WO | 2004074451 | 9/2004 |
| WO | 2004082638 | 9/2004 |
| WO | 2004087693 | 10/2004 |
| WO | 2004092115 | 10/2004 |
| WO | 2004103358 | 12/2004 |
| WO | 2005000901 | 1/2005 |
| WO | 2005023179 | 3/2005 |
| WO | 2005063806 | 7/2005 |
| WO | 2006012688 | 2/2006 |
| WO | 2006064121 | 6/2006 |
| WO | 2006082428 | 8/2006 |
| WO | 2006120456 | 11/2006 |
| WO | 2007049262 | 5/2007 |
| WO | 2007110623 | 10/2007 |
| WO | 2008090534 | 7/2008 |

OTHER PUBLICATIONS

Aravantinos G. et al., "Phase II study of docetaxel-vinorelbine in platinum-resistant, paclitaxel-pretreated ovarian cancer." Ann. Oncol., Jul. 2003; 14(7): 1094-1099.

Arnold, N.B. et al., "The Histone Deacetylase Inhibitor Suberoylanilide Hydroxamic Acid Induces Growth Inhibition and Enhances Gemcitabine-Induced Cell Death in Pancreatic Cancer", Clin. Cancer Res., (2007), vol. 13, pp. 18-26.

Banwell, C.M. et al., "Targeting 1alpha,25-dihydroxyvitamin D3 Antiproliferative Insensitivity in Breast Cancer Cells by Co-Treatment with Histone Deacetylation Inhibitors", Journal of Steroid Biochemistry & Molecular Biology, (2004), vol. 89-90, pp. 245-249.

Baradari, V. et al., "Histone Deacetylase Inhibitor MS-275 Alone or Combined with Bortezomib or Sorafenib Exhibits Strong Antiproliferative Action in Human Cholangiocarcinoma Cells", World Journal of Gastroenterology, (Sep. 7, 2007), vol. 13, No. 33, pp. 4458-4466.

Bast, R.C. et al. "Chapter 321: Ovarian Cancer"; Harrison's Principles of Internal Medicine, 13th Ed., Isselbacher et al., eds., McGraw-Hill, NY, 1853-1858, (1994).

Berenbaum et al., "What is Synergy?" Pharmacological Reviews, Jun. 1989; 41(2): 93-141.

Berge, S. et al. "Pharmaceutical Salts." J. Pharm. Sci., Jan. 1977; 66(1): 1-19.

Bolden, J. E. et al., "Anticancer activities of histone deacetylase inhibitors," Nat. Rev. Drug Discov., Sep. 2006, vol. 5, No. 9, pp. 769-784.

Bookman, M.A., "Extending the Platinum-Free Interval in Recurrent Ovarian Cancer: The Role of Topotecan in Second-Line Chemotherapy", The Oncologist, (1999), vol. 4, No. 2, pp. 87-94.

Budillon, A. et al. "Multiple-Target Drugs: Inhibitors of Heat Shock Protein 90 and of Histone Deacetylase." Curr. Drug Targets, 2005; 6(3):337-351.

Byers, T. "What Can Randomized Controlled Trials Tell Us About Nutrition and Cancer Prevention?" CA Cancer J. Clin., Nov.-Dec. 1999; 49(6):353-361.

Chou T. C. "Theoretical basis, experimental design, and computerized simulation of synergism and antagonism in drug combination studies." Pharmacol. Rev. Sep. 2006; 58(3): 621-81.

Dalgard, C.L. et al., "Evaluation of the In vitro and In vivo Antitumor Activity of Histone Deacetylase Inhibitors for the Therapy of Retinoblastoma", Clinical Cancer Research, (2008), vol. 14, pp. 3113-3123.

De Los Santos, M. et al., "Anti-estrogenic Actions of Histone Deacetylase Inhibitors in MCF-7 Breast Cancer Cells", Endocrine-Related Cancer, (2007), vol. 14, pp. 1021-1028.

De Ruijter, A.J.M. et al., "Antagonistic Effects of Sequential Administration of BL1521, a Histone Deacetylase Inhibitor, and Gemcitabine to Neuroblastoma Cells", Cancer Letters, (2006), vol. 233, No. 2, pp. 240-246.

Döwald et al., "Side reactions in organic synthesis: A guide to successful synthesis design," Weinheim: WILEY-VCH Verlag GmbH & Co. KgaA, 2005, Preface.

Entin-Meer, M. et al., "AN-113, a Novel Prodrug of 4-Phenylbutyrate with Increased Anti-neoplastic Activity in Glioma Cell Lines", (2007), vol. 253, pp. 205-214.

Granziero, L. et al. "Adoptive immunotherapy prevents prostate cancer in a transgenic animal model." Eur. J. Immunol., Apr. 1999; 29(4):1127-1138.

Hamilton T. C. et al., "Characterization of a human ovarian carcinoma cell line {NIH:OVCAR-3) with androgen and estrogen receptors." Cancer Res. Nov. 1983; 43(11): 5379-89.

Havrilesky, L.J. et al. "Weekly low-dose carboplatin and paclitaxel in the treatment of recurrent ovarian and peritoneal cancer." Gynecological Cancer; May 2003; 88(1): 51-57.

Hurtubise, A. et al., "Effect of Histone Deacetylase Inhibitor LAQ824 on Antineoplastic Action of 5-Aza-2'-deoxycytidine (Decitabine) on Human Breast Carcinoma Cells", Cancer Chemother. Pharmacol., (2006), vol. 58, pp. 618-625.

Jang, E.-R. et al., "Different Effect of Protein Kinase B/Akt and Extrcellular Signal-Regulated Kinase Inhibition on Trichostatin A-Induced Apoptosis in Epithelial Ovarian Carcinoma Cell Lines", Mol. Cell Biochem., (2011), vol. 353, pp. 1-11.

Jensen, P.B. et al. "Differential cytotoxicity of 19 anticancer agents in wild type and etoposide resistant small cell lung cancer cell lines." Br. J. Cancer, 1993; 67(2): 311-320.

Jordan, V.C. "Tamoxifen: A Most Unlikely Pioneering Medicine." Nat Rev Drug Discov., Mar. 2003; 2(3): 205-213.

Kano, Y. et al., "Cytotoxic Effects of Histone Deacetylase Inhibitor FK228 {Depsipeptide, formerly named FR901228) in Combination with Conventional Anti-Leukemia/Lymphoma Agents Against Human Leukemia/Lymphoma Cell Lines", Invest. New Drugs, {2006), vol. 25, pp. 31-40.

(56) References Cited

OTHER PUBLICATIONS

Khan, S.B. et al., "Analysis of Histone Deacetylase Inhibitor, Depsipeptide (FR901228), Effect on Multiple Myeloma", British Journal of Haematology, (2004), vol. 125, pp. 156-161.

Kim, J.C. et al., "In Vitro Evaluation of Histone Deacetylase Inhibitors as Combination Agents for Colorectal Cancer", Anticancer Research, (2009), vol. 29, pp. 3027-3034.

Knies-Bamforth, U. "Fight against cancer taking centre stage in Boston." Drug Discovery Today, Elsevier Science Limited, GB, 2004; 9(23):998-999.

Kuzuya K. et al., "Optimal doses of paclitaxel and carboplatin combination chemotherapy for ovarian cancer: a phase I modified continual reassessment method study." Int. J. Clin. Oncol. Dec. 2001; 6(6): 271-8.

Lai, J.-P. et al., "Additive Effect of Apicidin and Doxorubicin in Sulfatase 1 Expressing Hepatocellular Carcinoma In Vitro and In vivo", Journal of Hepatology, vol. 50, pp. 1112-1121, (2009).

Li, P. et al., "Coordination of PAD4 and HDAC2 in the Regulation of p53-Target Gene Expression", (2010), vol. 29, pp. 3153-3162.

Moradei, O. et al. "Histone Deacetylase Inhibitors: Latest Developments, Trends and Prospects." Curr. Med. Chem.—Anti-Cancer Agents, 2005; 5(5):529-560.

Neijt, J.P. et al. "Paclitaxel/carboplatin for the initial treatment of advanced ovarian cancer." Seminars in Oncology, Feb. 1999; 26(2 Suppl.): 78-83.

Ozols, R.F. "Recurrent Ovarian Cancer: Evidence-based Treatment." J. Clin. Oncol., Mar. 2002; 20(5): 1161-1163.

Paris M. et al., "Histone deacetylase inhibitors: from bench to clinic." J Med Chem. Mar. 27, 2008; 51(6):1505-29. Epub Feb. 5, 2008.

Pauer, L.R. et al. "Phase I Study of Oral CI-994 in Combination with Carboplatin and Paclitaxel in the Treatment of Patients with Advanced Solid Tumors." Cancer Investigation, 2004; 22(6):886-896.

Peng, C.-Y. et al., "Growth-Inhibiting Effects of Arsenic Trioxide Plus Epigenetic Therapeutic Agents on Leukemia Cell Lines", Leukemia & Lymphoma, (Feb. 2010), vol. 51, No. 2, pp. 297-303.

Plumb, J.A. et al. "Epigenetic approaches to cancer therapy." Biochem. Soc. Transactions, 2004; 32(6):1095-1097.

Plumb, J. A. et al., "Pharmacodynamic response and inhibition of growth of human tumor xenografts by the novel histone deacetylase inhibitor PXD101," Mol. Cancer Ther., Aug. 2003, vol. 2, No. 8, pp. 721-728.

Ritchie, J. et al., "The histone deacetylase inhibitor PXD101 synergises with established chemotherapeutics to inhibit tumor cell proliferation and upregulate apoptosis in vitro," Clinical Cancer Res., Dec. 2003, vol. 9, No. 16, Supplement, pp. 6105S-6106S, Abstract # A150.

Rovida, E. et al., "The c-Jun-N-terminal-Kinase Inhibitor SP600125 Enhances the Butyrate Derivative D1-Induced Apoptosis Via Caspase 8 Activation in Kasumi 1 t(8;21) Acute Myeloid Leukaemia Cells", British Journal of Haematology, (2006), vol. 135, pp. 653-659.

Shabbeer, S. et al. "Focus on deacetylation for therapeutic benefit." IDrugs, 2005; 8(2): 144-154.

Sonnemann, J. et al., "Comparative Evaluation of the Treatment Efficacy of Suberoylanilide Hydroxamic Acid (SAHA) and Paclitaxel in Ovarian Cancer Cell Lines and Primary Ovarian Cancer Cells from Patients", BMC Cancer, (2006), vol. 6, pp. 183.

Taddei, A. et al., "The Effects of Histone Deacetylase Inhibitors on Heterochromatin: Implications for Anticancer Therapy", EMBO Reports, (2005), vol. 6, No. 6, pp. 520-524.

Thigpen J. T. et al., Second-line chemotherapy for recurrent carcinoma of the ovary. Cancer. Feb. 15, 1993; 71(4 Suppl):1559-64.

Touma, S.E. et al., "Retinoic Acid and the Histone Deacetylase Inhibitor Trichostatin A Inhibit the Proliferation of Human Renal Cell Carcinoma in a Xenograft Tumor Model", Clinical Cancer Research, (2005), vol. 11, pp. 3558-3566.

Vasey, P. et al. "Phase III Randomized Trial of Docetaxel-Carboplatin Versus Paclitaxel-Carboplatin as First-line Chemotherapy for Ovarian Carcinoma." J. Natl. Cancer Inst., Nov. 2004; 96(22): 1682-1691.

Vippagunta, S. R. et al., "Crystalline solids," Adv. Drug Deliv. Rev., May 16, 2001, vol. 48, No. 1, pp. 3-26, pp. 18.

Wedel, S. et al., "Inhibitory Effects of the HDAC Inhibitor Valproic Acid on Prostrate Cancer Growth Are Enhanced by Simultaneous Application of mTOR Inhibitor RAD001", Life Sciences, (2011), vol. 88, pp. 418-424.

Bernstein, B. E. et al., Genomewide studies of histone deacetylase function in yeast. Proc Natl Acad Sci U S A. Dec. 5, 2000, vol. 97, No. 25, pp. 13708-13713. Erratum in: Proc Natl Acad Sci U S A Apr. 24, 2001, vol. 98, No. 9, pp. 5368.

Brehm, A. et al. "Retinoblastoma Protein Recruits Histone Deacetylase to Repress Transcription." Nature, 1998; 391:597-601.

Chang et al. "Activation of the BRLF1 Promoter and Lytic Cycle of Epstein-Barr Virus by Histone Acetylation." Nucleic Acids Res., 2000; 28(20):3918-3925.

Dangond et al. "Differential Display Cloning of a Novel Human Histone Deacetylase (HDAC3) cDNA from PHA-Activated Immune Cells." Biochem. Biophys. Res. Commun., 1998; 242(3): 648-652.

David, G. et al. "Histone Deacetylase Associated with mSin3A Mediates Repression by the Acute Promyelocytic Leukemia-associated PLZF Protein." Oncogene, 1998; 16(19): 2549-2556.

Davie, J.R. "Covalent Modifications of Histones: Expression from Chromatic Templates." Curr. Opin. Genet. Dev., 1998; 8(2): 173-178.

Emiliani, s. et al. "Characterization of a Human RPD3 Ortholog, HDAC3." Proc. Natl. Acad. Sci. USA, 1998; 95(6): 2795-2800.

Finnin et al. "Structures of a Histone Deacetylase Homologue Bound to the TSA and SAHA Inhibitors." Nature, 1999; 401(6749): 188-193.

Grozinger et al. "Three Proteins Define a Class of Human Histone Deacetylase Related to Yeast Hdalp." Proc. Natl. Acad. Sci. USA, 1999; 96(9): 4868-4873.

Hirano, A et al. "Application of Arginine to Increase the Solubility of Poorly Water-Soluble Compounds." J. of Proteomics & Bioinformatics, Proceedings of the Joint 2nd Pacific Rim International conference on Protein Science and 4th Asian-Oceania Human Proteome Organization, Cairns, Australia, Jun. 22-26, Abstract No. 220.

Hockly, E. et al. "Suberoylanilide Hydroxamic Acid, a Histone Deacetylase Inhibitor, Ameliorates Motor Deficits in a Mouse Model of Huntington's Disease." Proc. Natl. Acad. Sci. USA, 2003; 100(4): 2041-2046.

Hoshikawa, Y. et al. "Trichostatin A Induces Morphological Changes and Gelsolin Expression by Inhibiting Histone Deacetylase in Human Carcinoma Cell Lines." Exp. Cell. Res., 1994; 214(1): 189-197.

Howe, L. et al. "Histone Acetyltransferase Complexes and Their Link to Transcription." Crit. Rev. Eukaryot. Gene Expr., 1999; 9(3-4): 231-243.

Iavarone et al. "E2F and Histone Deacetylase Mediate Transforming Growth Factor β Repression of cdc25A During Keratinocyte Cell Cycle Arrest." Mol. Cell Biol., 1999; 19(1):916-922.

Kao, H.Y. et al., "Isolation of a novel histone deacetylase reveals that class I and class II deacetylases promote SMRT-mediated repression," Genes Dev., Jan. 1, 2000, vol. 14, No. 1, pp. 55-66.

Kasim, N.A. et al. "Molecular Properties of WHO Essential Drugs and Provisional Biopharmaceutical Classification." Mol. Pharma, Sep. 2003; 1(1): 85-96.

Kim, Y.B. et al. "Oxamflatin is a Novel Antitumor Compound that Inhibits Mammalian Histone Deacetylase." Oncogene, 1999; 18(15): 2461-2470.

Kim, M.S. et al. "Histone Deacetylases Induce Angiogenesis by Negative Regulation of Tumour Suppressor Genes." Nature Medicine, 2001; 7(4):437-443.

Kimura et al. "Dual Modes of Action of Platelet-Derived Growth Factor and its Inhibition by Trichostatin-A for DNA Synthesis in Primary Cultured Smooth Muscle Cells of Rat Aorta." Biol. Pharm. Bull., 1994; 17(3):399-402.

(56) References Cited

OTHER PUBLICATIONS

Kitamura, K. et al. "Histone Deacetylase Inhibitor But Not Arsenic Trioxide Differentiates Acute Promyelocytic Leukemia Cells with t(11;17) in Combination with All-Trans Retinoic Acid." Br. J. Haematol., 2000; 108(4):696-702.
Kouzarides, T. "Histone Acetylases and Deacetylases in Cell Proliferation." Curr. Opin. Genet. Dev., 1999; 9(1):40-48.
Kuusisto et al. "Ubiquitin-Binding Protein p62 Expression is Induced during Apoptosis and Proteasomal Inhibition in Neuronal Cells." Biochem. Biophys. Res. Commun., 2001; 280(1): 223-228.
Laherty, C.D. et al. "Histone Deacetylases Associated with the mSin3 Corepressor Mediate Mad Transcriptional Repression." Cell, May 1997; 89(3): 349-356.
Lin, R.J. et al. "Role of the Histone Deacetylase Complex in Acute Promyelocytic Leukaemia." Nature, Feb. 1998; 391 (6669): 811-814.
McCaffrey et al. "Induction of γ-Globin by Histone Deacetylase Inhibitors." Blood, Sep. 1997; 90(5):2075-2083.
Mielnicki et al. "Epigenetic Regulation of Gelsolin Expression in Human breast Cancer Cells." Exp. Cell. Res., 1999; 249(1):161-176.
Mura, P. et al. "Ternary systems of faproxen with hydroxypropyl-beta-cyclodextrin and aminoacids." Intl. J. Pharm., 2003; 260(2): 293-302.
Murata, T. et al., "Solubility of monoalkyl phosphate in water in the presence of arginine and triton, and solubilization of methyl yellow through the mixed micelle," Phosphorus Research Bulletin, (2008), vol. 22, pp. 41-47.
Ng, H.H. et al. "Histone Deacetylases: Silencers for Hire." Trends Biochem. Sci., 2000; 25(3):121-126.
Niki et al. "A Histone Deacetylase Inhibitor, Trichostatin A, Suppresses Myofibroblastic Differentiation of Rat Hepatic Stellate Cells in Primary Culture." Hepatol., 1999; 29(3):858-867.
Onishi et al. "Antibacterial Agents that Inhibit Lipid A Biosynthesis." Science, Nov. 1996; 274(5289): 939-940.
Pazin, M.J. et al. "What's Up and down with Histone Deacetylation and Transcription?" Cell, 1997; 89(3):325-328.
Saunders, N. et al. "Histone Deacetylase Inhibitors as Potential Anti-Skin Cancer Agents." Cancer Res., 1999; 59(2):399-404.
Spencer, V.A. et al. "Role of Covalent Modifications of Histones in Regulating Gene Expression." Gene, 1999; 240(1):1-12.
Strickley, R. G., "Solubilizing excipients in oral and injectable formulations," Pharm. Res., Feb. 2004, vol. 21, No. 2, pp. 201-230.
Takahashi, I. et al. "Selective Inhibition of IL-2 Gene Expression by Trichostatin A, a Potent Inhibitor of Mammalian Histone Deacetylase." J. Antibiot. {Tokyo), 1996; 49(5):453-457.
Taunton, J. et al. "A Mammalian Histone Deacetylase Related to the Yeast Transcriptional Regulator Rpd3p." Science, 1996; 272(5260): 408-411.
Tsuji et al. "A New Antifungal Antibiotic, Trichostatin." J. Antibiot. (Tokyo), 1976; 29(1):1-6.
Ueda, H. et al. "FR901228, a Novel Antitumor Bicyclic Depsipeptide Produced by Chromobacterium Violaceum No. 968." J. Antibiot. (Tokyo), 1994; 47(3):315-323.
Van Den Wyngaert et al., "Cloning and characterization of human histone deacetylase 8," FEBS L., 2000, Vo. 478, No. 1-2, pp. 77-83.
Vigushin et al. "Trichostatin A Is a Histone Deacetylase Inhibitor with Potent Antitumor Activity against Breast Cancer in vivo." Clin. Cancer Res., 2001; 7(4):971-976.
Wolff, et al.: Burger's Medicinal Chemistry and Drug Discovery—Fifth Ed. New York: John Wiley & Sons, 1996; vol. 1, pp. 975-977.
Wong, J. et al. "Distinct Requirements for Chromatin Assembly in Transcriptional Repression by Thyroid Hormone Receptor and Histone Deacetylase." EMBO J., 1998; 17(2):520-534.
Yang, W.M. et al. "Transcriptional Repression of YY1 is Mediated by Interaction with a Mammalian Homolog of the Yeast Global Regulator RPD3." Proc. Natl. Acad. Sci. USA, 1996; 93(23): 12845-12850.
Yang, W.M. et al. "Isolation and Characterization of cDNAs Corresponding to an Additional Member of the Human Histone Deacetylase Gene Family." J. Biol. Chem., 1997; 272(44): 28001-28007.

Yoshida, M. et al. "Trichostatin and leptomycin: inhibition of histone deacetylation and signal-dependent nuclear export." Ann. Ny. Y. Acad. Sci., 1999; 886: 23-36.
Yoshida, M. et al. "Reversible Arrest of Proliferation of rat 3Y1 Fibroblasts in Both G1 and G2 Phases by Trichostatin A." Exp. Cell. Res., 1988; 177(1): 122-131.
Yoshida, M. et al. "Potent and Specific Inhibition of Mammalian Histone Deacetylase Both in Vivo and in Vitro by Trichostatin A." J. Biol. Chem, 1990; 265(28):17174-17179.
Yoshida, M. et al. "Structural Specificity for Biological Activity of Trichostatin A, a Specific Inhibitor of Mammalian Cell Cycle with Potent Differentiation-Inducing Activity in Friend Leukemia Cells." J. Antibiot. (Tokyo), 1990; 43(9):1101-1106.
Zenger, M. et al. "Chapter 27: Structure-Activity Relationship and Drug Design." Remington's Pharmaceutical Sciences, 16th Ed. (1980): pp. 420-425.
Wingo, P .A. et al. "Cancer Statistics." CA Cancer J. Clin., 1995; 45(1): 8-30.
Yang et al. "Knockdown of Rab25 expression by RNAi inhibits growth of human epithelial ovarian cancer cells in vitro and in vivo." Pathology, Dec. 2006; 38(6): 561-567.
Zhao, J.-Y. et al., "SAHA and Curcumin Combinations Co-Enhance Histone Acetylation in Human Cancer Cells But Operate Antagonistically in Exerting Cytotoxic Effects", Journal of Asian Natural Products Research, (May 2010), vol. 12, No. 5, pp. 335-348.
"Guidance for Industry: S1C(R2) Dose selection for carcinogenicity studies," U.S. Department of Health and Human Services, Food and Drug Administration, Center for Drug Evaluation and Research (CDER), Center for Biologics Evaluation and Research (CBER), Sep. 2008.
"Topotarget Aims for Top of Class," Bioventure View (2004); 19(13):11.
"TopoTarget and CuraGen advance HDAC inhibitor PXD101 into Phase II clinical trials," Press Release dated Feb. 1, 2005 and retrieved from the Internet 2006 (URL: http://www.topotarget.com/Multimedia/19-_pressrelease_01022005.pdf).
American Cancer Society, Inc., "Cancer Facts and Figures 2003," 2003; pp. 1-52.
Andrews et al. "Anti-malarial Effect of Histone Deacetylation Inhibitors and Mammalian Tumour Cytodifferentiating Agents." Int. J. Parasitol., 2000; 30(6): 761-768.
Bernhard, D. et al. "Apoptosis Induced by the Histone Deacetylase Inhibitor Sodium Butyrate in Human Leukemic Lymphoblasts." FASEB J., 1999; 13(14): 1991-2001.
Bouchain G et al, 2003, "Development of potential antitumor agents, synthesis and biological evaluation of a new set of sulphonamide derivatives as histone deacetylase inhibitors", J. Med. Chem., vol. 46, pp. 820-830.
Finn, P W et al, 2005, "Novel sulphonamide derivatives as inhibitors of histone deacetylase", Helvetica Chimica Acta, vol. 88, pp. 1630-1657.
International Search Report and Written Opinion for PCT/GB2008/003226 mailed May 13, 2009.
International Preliminary Report on Patentability for PCT/GB2008/003226 issued Mar. 30, 2010.
Moore, P.S. et al., "Gene expression profiling after treatment with the histone deacetylase inhibitor trichostatin A reveals altered expression of both pro- and anti-apoptotic genes in pancreatic adenocarcinoma cells," Biochem. Biophys. Acta., Sep. 17, 2004, vol. 1693, No. 3, pp. 167-176.
Stapnes, C. et al., "Functional characteristics and gene expression profiles of primary acute myeloid leukaemia cells identify patient subgroups that differ in susceptibility to histone deacetylase inhibitors," Int. J. Oncol., Dec. 2007, vol. 31, No. 6, pp. 1529-1538.
Yamagishi, S. et al., "Expression of dihydropyrimidine dehydrogenase, thymidylate synthase, p53 and p21 in metastatic liver tumor from colorectal cancer after 5-fluorouracil-based chemotherapy," Anticancer Res., Mar.-Apr. 2005, vol. 25, No. 2B, pp. 1237-1242.
Lee, J.H. et al. "Histone deacetylase inhibitor enhances 5-fluorouracil cytotoxicity by down-regulating thymidylate synthase in human cancer cells." Mol. Cancer Ther., Dec. 2006; 5(12): 3085-3095.

(56) References Cited

OTHER PUBLICATIONS

Gimsing, P. et al., A phase I clinical trial of the histone deacetylase inhibitor belinostat in patients with advanced hematological neoplasia. Eur J Haematol. Sep. 2008, vol. 81, No. 3, pp. 170-176.

Steele, N. L. et al., A phase 1 pharmacokinetic and pharmacodynamic study of the histone deacetylase inhibitor belinostat in patients with advanced solid tumors. Clin. Cancer Res. Feb. 1, 2008, vol. 14, No. 3, pp. 804-810.

Advani, R. et al., 2007, "Belinostat (PXD101) in patients with recurrent or refractory peripheral or cutaneous T-cell lymphoma: results of a phase II study," American Society for Hematology, vol. 110, Abstract No. 3453.

Avis, K.E. et al. (editors), 1992, "Pharmaceutical Dosage Forms: parenteral medications," second edition, pp. 514-518.

Gimseng et al., 2005, "Activity of the histone deacetylase (HDAC) inhibitor PXD101 in preclinical studies and in a phase I study in patients with advanced hematological tumors," American Society of Hematology, vol. 106, Abstract No. 3337.

Gimseng, P. et al., 2009, "Belinostat: a new broad acting antineoplastic histone deacetylase inhibitor," Expert Opin. Investig, Drugs, vol. 18, pp. 501-508.

Mackay, H. J. et al., 2007, "A phase II trial of the histone deacetylase inhibitor belinostat (PXD101) in patients with platinum resistant epithelial ovarian tumors and micropapillary/borderline (LMP) ovarian tumors. A trial of the PMH phase II consortium," AACR-NCI-EORTC Annual Meeting 2007, American Association for Cancer Research: Molecular Targets and Cancer Therapeutics.

Sinha et al., 2007, "A phase I/II study of the safety and anticancer activity of IV-administered belinostat (PXD101) plus carboplatin (C) or paclitaxel (P), or both in patients with advanced solid tumours," 2007 Annual Meeting of the American Society of Clinical Oncology, Abstract No. 3574.

Sullivan, D. et al., 2006, "A Phase II Study of PXD101 in Advanced Multiple Myeloma," 2006, Annual Meeting of the American Society for Hematology, 2006, ASH Annual Meeting Abstracts, Part 1, vol. 108, Abstract 3583.

\* cited by examiner

METHODS OF SYNTHESIS OF CERTAIN HYDROXAMIC ACID COMPOUNDS

RELATED APPLICATION

This application is a 35 U.S.C. §371 national phase application of PCT/GB2008/003226 (WO 2009/040517), filed on Sep. 23, 2008, entitled "Methods of Synthesis of Certain Hydroxamic Acid Compounds." which application claims the benefit of U.S. provisional patent application No. 60/974,880 filed 25 Sep. 2007, the contents of which are incorporated herein by reference in their entirety.

TECHNICAL FIELD

The present invention pertains to the general field of chemical synthesis, and more particularly to methods for the synthesis of certain hydroxamic acid compounds, and in particular, (E)-N-hydroxy-3-(3-phenylsulfamoyl-phenyl)-acrylamide, also known as PXD101 and Belinostat®.

BACKGROUND

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

PXD101/Belinostat®

(E)-N-hydroxy-3-(3-phenylsulfamoyl-phenyl)-acrylamide, also known as PXD101 and Belinostat®, shown below, is a well known histone deacetylate (HDAC) inhibitor. It is being developed for treatment of a range of disorders mediated by HDAC, including proliferative conditions (such as cancer and psoriasis), malaria, etc.

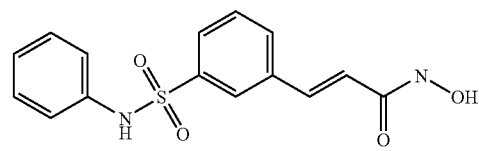 [SMILES: O=C(/C=C/c1cccc(S(=O)(=O)Nc2ccccc2)c1)NO]

PXD101 was first described in WO 02/30879 A2. That document describes a multi-step method of synthesis which may conveniently be illustrated by the following scheme.

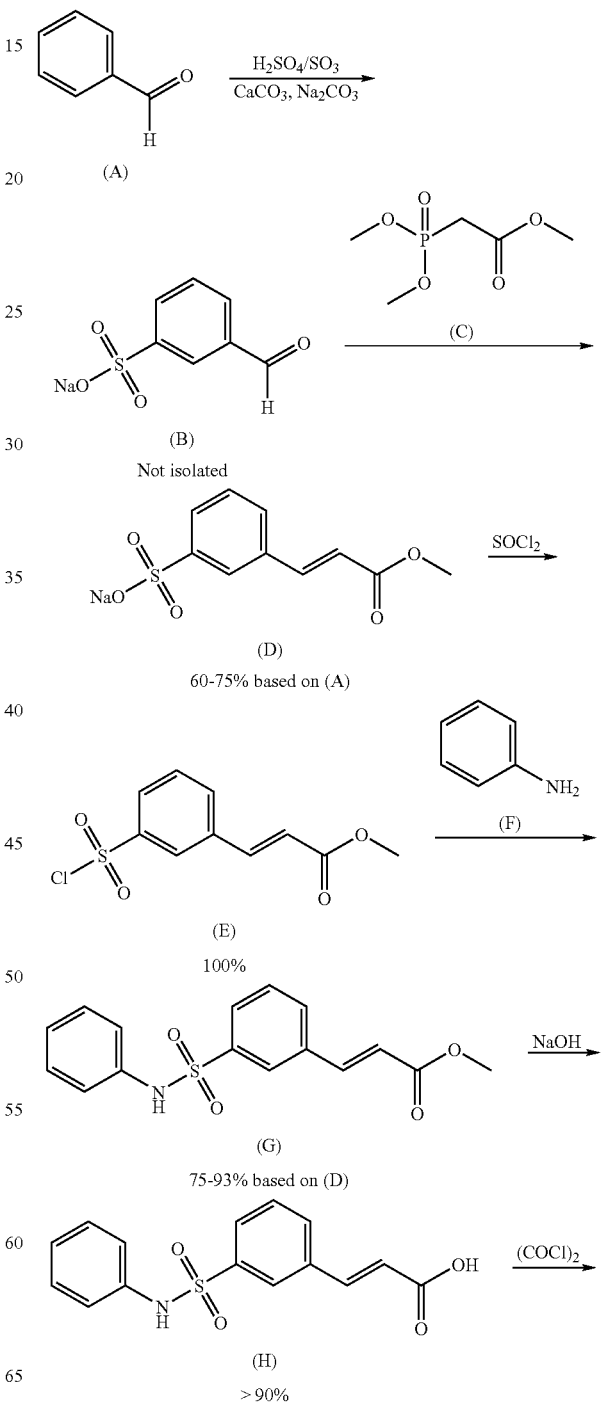

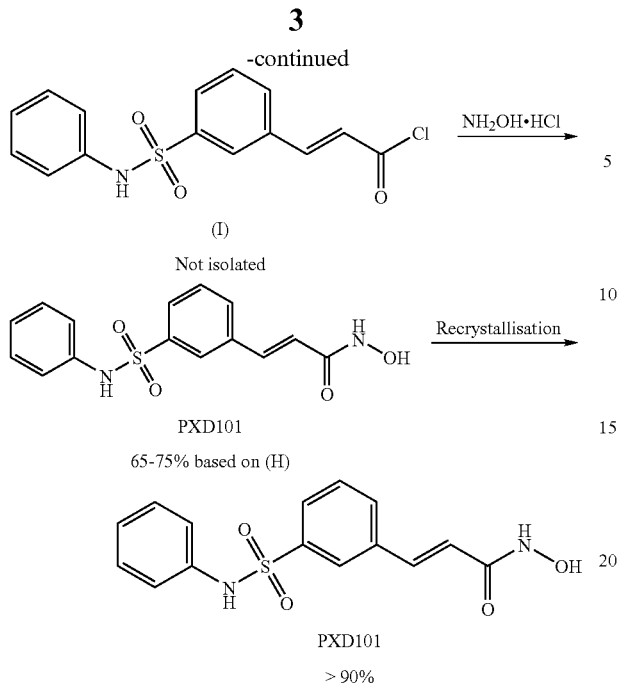

(I)
Not isolated

PXD101
65-75% based on (H)

PXD101
>90%

There is a need for alternative methods for the synthesis of PXD101 and related compounds for example, methods which are simpler and/or employ fewer steps and/or permit higher yields and/or higher purity product.

SUMMARY OF THE INVENTION

One aspect of the present invention pertains to certain methods for the synthesis of compounds of the Formula (G) and salts, hydrates, and solvates thereof, as described herein.

Another aspect of the present invention pertains to methods for the synthesis of corresponding chemical intermediates, including compounds of Formulas (C), (E), and (F), and salts, hydrates, and solvates thereof, from which compounds of Formula (G) may be prepared, as described herein.

Another aspect of the present invention pertains to certain compounds, including compounds for Formulae (C), (E), (F), and (G), and salts, hydrates, and solvates thereof, obtained by a method of synthesis, as described herein.

Another aspect of the present invention pertains to a compound of Formula (G) obtained by a method of synthesis, as described herein, for use in a method of treatment of the human or animal body.

Another aspect of the present invention pertains to a compound of Formula (G) obtained by a method of synthesis, as described herein, for use in a method of treatment of a disease or disorder which is mediated by HDAC.

Another aspect of the present invention pertains to use of a compound of Formula (G) obtained by a method of synthesis, as described herein, in the manufacture of a medicament for the treatment of a disease or disorder which is mediated by HDAC.

Another aspect of the present invention pertains to a method of treatment of a disease or disorder which is mediated by HDAC in a patient, comprising administering to said patient a therapeutically-effective amount of a compound of Formula (G) obtained by a method of synthesis, as described herein.

As will be appreciated by one of skill in the art, features and preferred embodiments of one aspect of the invention will also pertain to other aspect of the invention.

DETAILED DESCRIPTION OF THE INVENTION

One aspect of the present invention pertains to methods for the synthesis of compounds of the Formula (G) and salts, hydrates, and solvates thereof:

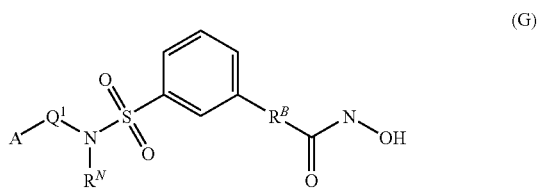

(G)

wherein:
-A is independently $-A^1$, $-A^2$, $-A^3$, or $-A^4$;
$-A^1$ is independently $C_{6-10}$carboaryl, and is optionally substituted;
$-A^2$ is independently $C_{5-10}$heteroaryl, and is optionally substituted;
$-A^3$ is independently $C_{5-7}$cycloalkyl, and is optionally substituted;
$-A^4$ is independently $C_{5-7}$heterocyclic, and is optionally substituted;
$-Q^1$- is independently a covalent bond or $-R^A-$,
$-R^A-$ is independently $-R^{A1}-$ or $-R^{A2}-$;
$-R^{A1}-$ is independently aliphatic $C_{2-6}$alkylene, and is optionally substituted;
$-R^{A2}-$ is independently aliphatic $C_{2-6}$alkenylene, and is optionally substituted;
$-R^N$ is independently $-H$, saturated aliphatic $C_{1-4}$alkyl, phenyl, or benzyl; and
$-R^B-$ is independently $-R^{B1}-$ or $-R^{B2}-$;
$-R^{B1}-$ is independently aliphatic $C_{2-6}$alkenylene, and is optionally substituted;
$-R^{B2}-$ is independently aliphatic $C_{2-6}$alkynyl-alkenylene, and is optionally substituted.

Another aspect of the present invention pertains to methods for the synthesis of corresponding chemical intermediates, including compounds of Formulas (C), (E), and (F), and salts, hydrates, and solvates thereof, for example, from which compounds of Formula (G) may be prepared, as described herein.

The Group -A

In one embodiment, -A is independently $-A^1$, $-A^2$, $-A^3$, or $-A^4$.

In one embodiment, -A is independently $-A^1$ or $-A^2$.
In one embodiment, -A is independently $-A^1$.
In one embodiment, -A is independently $-A^2$.
In one embodiment, -A is independently $-A^3$.
In one embodiment, -A is independently $-A^4$.
In one embodiment, $-A^1$ is independently $C_{6-10}$carboaryl, and is optionally substituted.
In one embodiment, $-A^1$ is independently phenyl or napthyl, and is optionally substituted.
In one embodiment, $-A^1$ is independently phenyl, and is optionally substituted.
In one embodiment, $-A^1$ is independently napthyl, and is optionally substituted.
In one embodiment, $-A^2$ is independently $C_{5-10}$heteroaryl, and is optionally substituted.
In one embodiment, $-A^2$ is independently furanyl, thienyl, pyrrolyl, imidazolyl, pyrazolyl, triazolyl, oxazolyl, isoxazoly, thiazolyl, isothiazolyl, pyridyl, pyrazinyl, pyrimidinyl, pyridazinyl, benzofuranyl, isobenzofuranyl, indazolyl, purinyl, quinolinyl, isoquinolinyl, naphthyridinyl, quinoxalinyl, quinazolinyl, cinnolinyl, indolyl, isoindolyl, carbazolyl, carbolinyl, acridinyl, phenoxazinyl, or phenothiazinyl, and is optionally substituted.

In one embodiment, -A$^2$ is independently C$_{5-6}$heteroaryl, and is optionally substituted.

In one embodiment, -A$^2$ is independently furanyl, thienyl, pyrrolyl, imidazolyl, pyrazolyl, triazolyl, oxazolyl, isoxazolyl, thiazolyl, isothiazolyl, pyridyl, pyrazinyl, pyrimidinyl, or pyridazinyl, and is optionally substituted.

In one embodiment, -A$^2$ is independently pyridyl, pyrazinyl, pyrimidinyl, pyridazinyl, or pyrazolyl, and is optionally substituted.

In one embodiment, -A$^2$ is independently pyridyl, and is optionally substituted.

In one embodiment, -A$^3$ is independently C$_{5-7}$cycloalkyl, and is optionally substituted.

In one embodiment, -A$^4$ is independently C$_{5-7}$heterocyclic, and is optionally substituted.

In one embodiment, -A is independently unsubstituted or substituted, for example, with one or more substitutents, for example, with one or more (e.g., 1, 2, 3) substituents —R$^{G1}$.

In one embodiment, -A is independently unsubstituted.

In one embodiment, -A is independently unsubtituted phenyl.

Substituents —R$^{G1}$

In one embodiment, each —R$^{G1}$, if present, is independently:
—F, —Cl, —Br, —I,
—R$^{H1}$,
—CF$_3$, —CH$_2$CF$_3$, —CF$_2$CF$_2$H, —OCF$_3$, —OCH$_2$CF$_3$, —OCF$_2$CF$_2$H,
—OH, -L$^H$-OH, —O-L$^H$-OH,
—OR$^{H1}$, -L$^H$-OR$^{H1}$, —O-L$^H$-OR$^{H1}$,
—SH, —SR$^{H1}$,
—CN,
—NO$_2$,
—NH$_2$, —NHR$^{H1}$, —NR$^{H1}{}_2$, —NR$^{H2}$R$^{H3}$,
-L$^H$-NH$_2$, -L$^H$-NHR$^{H1}$, -L$^H$-NR$^{H1}{}_2$, -L$^H$-NR$^{H2}$R$^{H3}$,
—O-L$^H$-NH$_2$, —O-L$^H$-NHR$^{H1}$, —O-L$^H$-NR$^{H1}{}_2$,
—O-L$^H$-NR$^{H2}$R$^{H3}$,
—NH-L$^H$-NH$_2$, —NH-L$^H$-NHR$^{H1}$, —NH-L$^H$-NR$^{H1}{}_2$,
—NH-L$^H$-NR$^{H2}$R$^{H3}$,
—NR$^{H1}$-L$^H$-NH$_2$, —NR$^{H1}$-L$^H$-NHR$^{H1}$, —NR$^{H1}$-L$^H$-NR$^{H1}{}_2$, —NR$^{H1}$-L$^H$-NR$^{H2}$R$^{H3}$,
—C(=O)OH, —C(=O)OR$^{H1}$,
—C(=O)NH$_2$, —C(=O)NHR$^{H1}$, —C(=O)NR$^{H1}{}_2$, —C(=O)NR$^{H2}$R$^{H3}$,
—NHC(=O)R$^{H1}$, —NR$^{H1}$C(=O)R$^{H1}$, —NHC(=O)OR$^{H1}$, —NR$^{H1}$C(=O)OR$^{H1}$,
—OC(=O)NH$_2$, —OC(=O)NHR$^{H1}$, —OC(=O)NR$^{H1}{}_2$, —OC(=O)NR$^{H2}$R$^{H3}$,
—OC(=O)R$^{H1}$,
—C(=O)R$^{H1}$,
—NHC(=O)NH$_2$, —NHC(=O)NHR$^{H1}$, —NHC(=O)NR$^{H1}{}_2$, —NHC(=O)NR$^{H2}$R$^{H3}$,
—NR$^{H1}$C(=O)NH$_2$, —NR$^{H1}$C(=O)NHR$^{H1}$, —NR$^{H1}$C(=O)NR$^{H1}{}_2$, —NR$^{H1}$C(=O)NR$^{H2}$R$^{H3}$,
—NHS(=O)$_2$R$^{H1}$, —NR$^{H1}$S(=O)$_2$R$^{H1}$,
—S(=O)$_2$NH$_2$, —S(=O)$_2$NHR$^{H1}$, —S(=O)$_2$NR$^{H1}{}_2$, —S(=O)$_2$NR$^{H2}$R$^{H3}$,
—S(=O)R$^{H1}$, —S(=O)$_2$R$^{H1}$, —OS(=O)$_2$R$^{H1}$, —S(=O)$_2$OR$^{H1}$,
=O,
=NRH$^{H1}$,
=NOH, or =NOR$^{H1}$;
and additionally, two ring adjacent groups —R$^{G1}$, if present, may together form a group —O-L$^J$-O—;

wherein:
each -L$^H$- is independently saturated aliphatic C$_{1-5}$alkylene;
each -L$^J$- is independently saturated aliphatic C$_{1-3}$alkylene;
in each group —NRH$^{H2}$R$^{H3}$, R$^{H2}$ and —R$^{H3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteratoms is independently N, O, or S;
each —R$^{H1}$ is independently:
—R$^{K1}$, —R$^{K2}$, —R$^{K3}$, —R$^{K4}$, —R$^{K5}$, —R$^{K6}$, —R$^{K7}$, —R$^{K8}$,
-L$^K$-R$^{K4}$, -L$^K$-R$^{K5}$, -L$^K$-R$^{K6}$, -L$^K$-R$^{K7}$, or -L$^K$-R$^{K8}$;
wherein:
each —R$^{K1}$ is independently saturated aliphatic C$_{1-6}$alkyl;
each —R$^{K2}$ is independently aliphatic C$_{2-6}$alkenyl;
each —R$^{K3}$ is independently aliphatic C$_{2-6}$alkynyl;
each —R$^{K4}$ is independently saturated C$_{3-6}$cycloalkyl;
each —R$^{K5}$ is independently C$_{3-6}$cycloalkenyl;
each —R$^{K6}$ is independently non-aromatic C$_{3-7}$heterocyclyl;
each —R$^{K7}$ is independently C$_{6-14}$carboaryl;
each —R$^{K8}$ is independently C$_{5-14}$heteroaryl;
each -L$^K$- is independently saturated aliphatic C$_{1-3}$alkylene;
and wherein:
each C$_{1-6}$alkyl, C$_{2-6}$alkenyl, C$_{2-6}$alkynyl, C$_{3-6}$cycloalkyl, C$_{3-6}$cycloalkenyl, non-aromatic C$_{3-7}$heterocyclyl, C$_{6-14}$carboaryl, C$_{5-14}$heteroaryl, and C$_{1-3}$alkylene is optionally substituted, for example, with one or more (e.g., 1, 2, 3) substituents —R$^{K9}$, wherein each —R$^{K9}$ is independently:
—F, —Cl, —Br, —I,
—R$^{M1}$,
—CF$_3$, —CH$_2$CF$_3$, —CF$_2$CF$_2$H, —OCF$_3$, —OCH$_2$CF$_3$, —OCF$_2$CF$_2$H,
—OH, -L$^M$-OH, —O-L$^M$-OH,
—OR$^{M1}$, -L$^M$-OR$^{M1}$, —O-L$^M$-OR$^{M1}$,
—SH, —SR$^{M1}$,
—CN,
—NO$_2$,
—NH$_2$, —NHR$^{M1}$, —NR$^{M1}{}_2$, —NR$^{M2}$R$^{M3}$,
-L$^M$-NH$_2$, -L$^M$-NHR$^{M1}$, -L$^M$-NR$^{M1}{}_2$, or -L$^M$-NR$^{M2}$R$^{M3}$,
—O-L$^M$-NH$_2$, —O-L$^M$-NHR$^{M1}$, —O-L$^M$-NR$^{M1}{}_2$,
—O-L$^4$-NR$^{M2}$R$^{M3}$,
—NH-L$^M$-NH$_2$, —NH-L$^M$-NHR$^{M1}$, —NH-L$^M$-NR$^{M1}{}_2$,
—NH-L$^M$-NR$^{M2}$R$^{M3}$,
—NR$^{M1}$-L$^M$-NH$_2$, —NR$^{M1}$-L$^M$-NHR$^{M1}$, —NR$^{M1}$-L$^M$-NR$^{M1}{}_2$, —NR$^{M1}$-L$^M$-NR$^{M2}$R$^{M3}$,
—C(=O)OH, —C(=O)OR$^{M1}$,
—C(=O)NH$_2$, —C(=O)NHR$^{M1}$, —C(=O)NR$^{M1}{}_2$, or —C(=O)NR$^{M2}$R$^{M3}$;
wherein:
each —R$^{M1}$ is independently saturated aliphatic C$_{1-4}$alkyl, phenyl, or benzyl;
each -L$^M$- is independently saturated aliphatic C$_{1-5}$alkylene; and
in each group —NR$^{M2}$R$^{M3}$, —R$^{M2}$ and —R$^{M3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteratoms is independently N, O, or S.

In one embodiment, each —$R^{G1}$, if present, is independently:
- —F, —Cl, —Br, —I,
- —$R^{H1}$,
- —$CF_3$, —$CH_2CF_3$, —$CF_2CF_2H$, —$OCF_3$, —$OCH_2CF_3$, —$OCF_2CF_2H$,
- —OH, -$L^H$-OH, —O-$L^H$-OH,
- —$OR^{H1}$, -$L^H$-$OR^{H1}$, —O-$L^H$-$OR^{H1}$,
- —SH, —$SR^{H1}$,
- —CN,
- —$NO_2$,
- —$NH_2$, —$NHR^{H1}$, —$NR^{H1}{}_2$, —$NR^{H2}R^{H3}$,
- -$L^H$-$NH_2$, -$L^H$-$NHR^{H1}$, -$L^H$-$NR^{H1}{}_2$, -$L^H$-$NR^{H2}R^{H3}$,
- —O-$L^H$-$NH_2$, —O-$L^H$-$NHR^{H1}$, —O-$L^H$-$NR^{H1}{}_2$, —O-$L^H$-$NR^{H2}R^{H3}$,
- —NH-$L^H$-$NH_2$, —NH-$L^H$-$NHR^{H1}$, —NH-$L^H$-$NR^{H1}{}_2$, —NH-$L^H$-$NR^{H2}R^{H3}$,
- —$NR^{H1}$-$L^H$-$NH_2$, —$NR^{H1}$-$L^H$-$NHR^{H1}$, —$NR^{H1}$-$L^H$-$NR^{H1}{}_2$, —$NR^{H1}$-$L^H$-$NR^{H2}R^{H3}$,
- —C(=O)OH, —C(=O)$OR^{H1}$,
- —C(=O)$NH_2$, —C(=O)$NHR^{H1}$, —C(=O)$NR^{H1}{}_2$, —C(=O)$NR^{H2}R^{H3}$,
- —NHC(=O)$R^{H1}$, —$NR^{H1}$C(=O)$R^{H1}$,
- —OC(=O)$R^{H1}$, —C(=O)$R^{H1}$,
- —NHS(=O)$_2R^{H1}$, —$NR^{H1}$S(=O)$_2R^{H1}$, —S(=O)$_2NH_2$, —S(=O)$_2NHR^{H1}$, —S(=O)$_2NR^{H1}{}_2$, or —S(=O)$_2NR^{H2}R^{H3}$, and additionally, two ring adjacent groups if present, may together form a group —O-$L^J$-O—.

In one embodiment, each group —$NR^{H2}R^{H3}$, if present, is independently pyrrolidino, imidazolidino, pyrazolidino, piperidino, piperizino, morpholino, thiomorpholino, azepino, or diazepino, and is independently unsubstituted or substituted, for example, with one or more (e.g., 1, 2, 3) groups selected from $C_{1-3}$alkyl and —$CF_3$.

In one embodiment, each group —$NR^{H2}R^{H3}$, if present, is independently pyrrolidino, piperidino, piperizino, or morpholino, and is independently unsubstituted or substituted, for example, with one or more (e.g., 1, 2, 3) groups selected from $C_{1-3}$alkyl and —$CF_3$.

In one embodiment, each —$R^{H1}$, if present, is independently:
- —$R^{K1}$, —$R^{K4}$, —$R^{K7}$, —$R^{K8}$,
- -$L^K$-$R^{K4}$, -$L^K$-$R^{K7}$, or -$L^K$-$R^8$.

In one embodiment, each —$R^{D1}$, if present, is independently:
- —$R^{K1}$, —$R^{K7}$, —$R^{K8}$, or -$L^K$-$R^{K7}$.

In one embodiment, each —$R^{D1}$, if present, is independently:
- —$R^{K1}$, —$R^{K7}$, or -$L^K$-$R^{K7}$.

In one embodiment, each —$R^{K7}$, if present, is independently phenyl or naphthyl; and is optionally substituted.

In one embodiment, each —$R^{K7}$, if present, is independently phenyl; and is optionally substituted.

In one embodiment, each —$R^{K8}$, if present, is independently furanyl, thienyl, pyrrolyl, imidazolyl, pyrazolyl, triazolyl, oxazolyl, isoxazoly, thiazolyl, isothiazolyl, pyridyl, pyrazinyl, pyrimidinyl, pyridazinyl, benzofuranyl, isobenzofuranyl, indazolyl, purinyl, quinolinyl, isoquinolinyl, naphthyridinyl, quinoxalinyl, quinazolinyl, cinnolinyl, indoly, isoindolyl, carbazolyl, carbolinyl, acridinyl, phenoxazinyl, or phenothiazinyl; and is optionally substituted.

In one embodiment, each —$R^{K8}$, if present, is independently $C_{5-6}$heteroaryl; and is optionally substituted.

In one embodiment, each —$R^{K8}$, if present, is independently furanyl, thienyl, pyrrolyl, imidazolyl, pyrazolyl, triazolyl, oxazolyl, isoxazoly, thiazolyl, isothiazolyl, pyridyl, pyrazinyl, pyrimidinyl, or pyridazinyl; and is optionally substituted.

In one embodiment, each —$R^{K8}$, if present, is independently furanyl, pyrrolyl, pyrazolyl, triazolyl, oxazolyl, isoxazoly, thiazolyl, isothiazolyl, or pyridyl; and is optionally substituted.

In one embodiment, each -$L^H$-, if present, is independently saturated aliphatic $C_{2-5}$alkylene.

In one embodiment, each -$L^J$-, if present, is independently —$CH_2$— or —$CH_2CH_2$—.

In one embodiment, each -$L^J$-, if present, is independently —$CH_2CH_2$—.

In one embodiment, each -$L^K$-, if present, is independently —$CH_2$—.

In one embodiment, each —$R^{K9}$, if present, is independently selected from:
- —F, —Cl, —Br, —I,
- —$R^{M1}$,
- —$CF_3$, —$CH_2CF_3$, —$CF_2CF_2H$, —$OCF_3$, —$OCH_2CF_3$, —$OCF_2CF_2H$,
- —OH, -$L^M$-OH, —O-$L^M$-OH,
- —$OR^{M1}$, -$L^M$-$OR^{M1}$, —O-$L^M$-$OR^{M1}$,
- —$SR^{M1}$,
- —$NH_2$, —$NHR^{M1}$, —$NR^{M1}{}_2$, —$NR^{M2}R^{M3}$,
- -$L^M$-$NH_2$, -$L^M$-$NHR^{M1}$, -$L^M$-$NR^{M1}{}_2$, or -$L^M$-$NR^{M2}R^{M3}$,
- —O-$L^M$-$NH_2$, —O-$L^M$-$NHR^{M1}$, —O-$L^M$-$NR^{M1}{}_2$, —O-$L^4$-$NR^{M2}R^{M3}$,
- —NH-$L^M$-$NH_2$, —NH-$L^M$-$NHR^{M1}$, —NH-$L^M$-$NR^{M1}{}_2$, —NH-$L^M$-$NR^{M2}R^{M3}$,
- —$NR^{M1}$-$L^M$-$NH_2$, —$NR^{M1}$-$L^M$-$NHR^{M1}$, —$NR^{M1}$-$L^M$-$NR^{M1}{}_2$, and —$NR^{M1}$-$L^M$-$NR^{M2}R^{M3}$.

In one embodiment, each group —$NR^{M2}R^{M3}$, if present, is independently pyrrolidino, imidazolidino, pyrazolidino, piperidino, piperizino, morpholino, thiomorpholino, azepino, or diazepino, and is independently unsubstituted or substituted, for example, with one or more (e.g., 1, 2, 3) groups selected from $C_{1-3}$alkyl and —$CF_3$.

In one embodiment, each group —$NR^{M2}R^{M3}$, if present, is independently pyrrolidino, piperidino, piperizino, or morpholino, and is independently unsubstituted or substituted, for example, with one or more (e.g., 1, 2, 3) groups selected from $C_{1-3}$alkyl and —$CF_3$.

In one embodiment, each —$R^{M1}$, if present, is independently saturated aliphatic $C_{1-4}$alkyl.

In one embodiment, each -$L^M$-, if present, is independently saturated aliphatic $C_{2-5}$alkylene.

In one embodiment, each —$R^{G1}$, if present, is independently —F, —Cl, —Br, —I, —OH, —OMe, —OEt, or —$OCF_3$; and additionally, two ring adjacent groups —$R^{G1}$, if present, may together form —O—$CH_2$—O— or —O—$CH_2CH_2$—O—.

The Group -$Q^1$-

In one embodiment:
-$Q^1$- is independently a covalent bond or —$R^A$—;
—$R^A$— is independently —$R^{A1}$— or —$R^{A2}$—;
—$R^{A1}$— is independently aliphatic $C_{2-6}$alkylene, and is optionally substituted; and
—$R^{A2}$— is independently aliphatic $C_{2-6}$alkenylene, and is optionally substituted.

The term "aliphatic $C_{1-n}$alkylene", as used herein, pertains to a divalent bidentate aliphatic hydrocarbyl group having from 1 to n carbon atoms and having no carbon-carbon double bonds and no carbon-carbon triple bonds.

The term "aliphatic $C_{2-n}$alkenylene", as used herein, pertains to a divalent bidentate aliphatic hydrocarbyl group having from 2 to n carbon atoms and having at least one carbon-carbon double bond, but no carbon-carbon triple bonds.

In one embodiment, -$Q^1$- is independently a covalent bond.

In one embodiment, -$Q^1$- is independently —$R^A$—.

In one embodiment, —$R^A$—, if present, is independently —$R^{A1}$— or —$R^{A2}$—.

In one embodiment, —$R^A$—, if present, is independently —$R^{A1}$—.

In one embodiment, —$R^A$—, if present, is independently —$R^{A2}$—.

In one embodiment, —$R^{A1}$—, if present, is independently aliphatic $C_{2-6}$alkylene, and is optionally substituted.

In one embodiment, —$R^{A1}$—, if present, is independently aliphatic $C_{1-4}$alkylene, and is optionally substituted.

In one embodiment, —$R^{A1}$—, if present, is independently aliphatic $C_{2-6}$alkenylene, and is optionally substituted.

In one embodiment, —$R^{A2}$—, if present, is independently aliphatic $C_{2-4}$alkenylene, and is optionally substituted.

In one embodiment, —$R^A$—, if present, independently has a backbone length of at least 2.

In one embodiment, —$R^A$—, if present, independently has a backbone length of from 2 to 6.

In one embodiment, —$R^A$—, if present, is independently unsubstituted or substituted, for example, with one or more substitutents, for example, with one or more (e.g., 1, 2, 3) substituents —$R^{G2}$.

In one embodiment, —$R^A$—, if present, is independently unsubstituted.

In one embodiment, —$R^{A1}$—, if present, is independently:
—$CH_2$—, —$CH_2CH_2$—, —$CH_2CH_2CH_2$—,
—$CH_2CH_2CH_2CH_2$—,
—$CH_2CH_2CH_2CH_2CH_2$—,
—$CH_2CH_2CH_2CH_2CH_2CH_2$—,
—$CH(CH_3)$—,
—$CH(CH_3)CH_2$—, —$CH_2CH(CH_3)$—,
—$CH(CH_3)CH_2CH_2$—, —$CH_2CH(CH_3)CH_2$—, or
—$CH_2CH_2CH(CH_3)$—.

In one embodiment, —$R^{A1}$—, if present, is independently:
—$CH_2CH_2$—, —$CH(CH_3)CH_2$—, or —$CH_2CH(CH_3)$—.

In one embodiment, —$R^{A2}$—, if present, is independently:
—$CH=CH$—,
—$C(CH_3)=CH$—, —$CH=C(CH_3)$—,
—$CH=CH—CH_2$—,
—$C(CH_3)=CH—CH_2$—, —$CH=C(CH_3)—CH_2$—,
—$CH=CH—CH(CH_3)$—,
—$CH=CH—CH=CH$—,
—$C(CH_3)=CH—CH=CH$—, —$CH=C(CH_3)—CH=CH$—,
—$CH=CH—C(CH_3)=CH$—, or —$CH=CH—CH=C(CH_3)$—.

In one embodiment, —$R^{A2}$—, if present, is independently:
—$CH=CH$—, —$C(CH_3)=CH$—, or —$CH=C(CH_3)$—.

Substituents —$R^{G2}$

In one embodiment, each —$R^{G2}$, if present, is independently —F, —Cl, —Br, —I, —OH, —$OR^{P1}$, —$OCF_3$, —C(=O)OH, —C(=O)$OR^{P1}$, —$NH_2$, —$NHR^{P1}$, —$NR^{P1}_2$, —$NR^{P2}R^{P3}$, —C(=O)—$NH_2$, —C(=O)—$NHR^{P1}$, —C(=O)—$NR^{P1}_2$, —C(=O)—$NR^{P2}R^{P3}$, phenyl, or benzyl; wherein each $R^{P1}$ is independently $C_{1-4}$alkyl, phenyl, or benzyl; and each —$NR^{P2}R^{P3}$ is independently pyrrolidino, piperidino, piperizino, or morpholino, and is independently unsubstituted or substituted with one or more groups selected from $C_{1-3}$alkyl and —$CF_3$.

In one embodiment, each —$R^{G2}$, if present, is independently —F, —Cl, —Br, —I, —OH, —OMe, —OEt, or —$OCF_3$.

The Group —$R^N$

In one embodiment, —$R^N$ is independently —H, saturated aliphatic $C_{1-4}$alkyl, phenyl, or benzyl.

In one embodiment, —$R^N$ is independently —H or saturated aliphatic $C_{1-4}$alkyl.

In one embodiment, —$R^N$ is independently —H, -Me, or -Et.

In one embodiment, —$R^N$ is independently —H or -Me.

In one embodiment, —$R^N$ is independently —H.

The Group —$R^B$—

In one embodiment:
—$R^B$— is independently —$R^{B1}$— or —$R^{B2}$—;
—$R^{B1}$— is independently aliphatic $C_{2-6}$alkenylene, and is optionally substituted;
—$R^{B2}$— is independently aliphatic $C_{2-6}$alkynyl-alkenylene, and is optionally substituted.

As mentioned above, the term "aliphatic $C_{2-n}$alkenylene", as used herein, pertains to a divalent bidentate aliphatic hydrocarbyl group having from 2 to n carbon atoms and having at least one carbon-carbon double bond, but no carbon-carbon triple bonds.

The term "aliphatic $C_{4-n}$alkynyl-alkenylene", as used herein, pertains to a divalent bidentate aliphatic hydrocarbyl group having from 4 to n carbon atoms and having at least one carbon-carbon double bond, and at least one carbon-carbon triple bond.

In one embodiment, —$R^B$— is independently —$R^{B1}$—.

In one embodiment, —$R^B$— is independently —$R^{B2}$—.

In one embodiment, —$R^{B1}$— is independently aliphatic $C_{2-6}$alkenylene, and is optionally substituted.

In one embodiment, —$R^{B1}$— is independently aliphatic $C_{2-4}$alkenylene, and is optionally substituted.

In one embodiment, —$R^B$— has a "leading" carbon-carbon double bond, that is, —$R^B$— has a carbon-carbon double bond adjacent to the phenylene ring (that is, the phenylene ring between the —S(=O)$_2$— group and —$R^B$—), for example, as in the following compound:

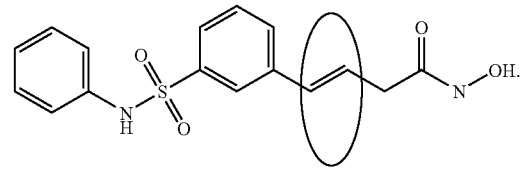 [SMILES: O=C(C/C=C/c1cccc(S(=O)(=O)Nc2ccccc2)c1)NO]

In one embodiment, —$R^{B1}$— is independently:
—$CH=CH$—,
—$C(CH_3)=CH$—, —$CH=C(CH_3)$—,
—$CH=CH—CH_2$—,
—$C(CH_3)=CH—CH_2$—, —$CH=C(CH_3)—CH_2$—,
—$CH=CH—CH(CH_3)$—,
—$CH=CH—CH=CH$—,
—$C(CH_3)=CH—CH=CH$—, —$CH=C(CH_3)—CH=CH$—,
—$CH=CH—C(CH_3)=CH$—, or —$CH=CH—CH=C(CH_3)$—.

In one embodiment, —$R^{B1}$— is independently:
—$CH=CH$—, —$CH=CH—CH_2$—, or —$CH=CH—CH=CH$—.

In one embodiment, —$R^{B1}$— is independently: —$CH=CH$—.

In one embodiment, —$R^{B2}$— is independently aliphatic $C_{2-6}$alkynyl-alkenylene, and is optionally substituted.

In one embodiment, —$R^{B2}$— is independently: —$CH=CH—C≡C$—.

In one embodiment, —$R^B$— is independently unsubstituted or substituted, for example, with one or more substitutents, for example, with one or more (e.g., 1, 2, 3) substituents —$R^{G3}$.

In one embodiment, —$R^B$— is independently unsubstituted.

Substituents —$R^{G3}$

In one embodiment, each —$R^{G3}$, if present, is independently —F, —Cl, —Br, —I, —OH, —$OR^{Q1}$, —$OCF_3$, —C(=O)OH, —C(=O)$OR^{Q1}$, —$NH_2$, —$NHR^{Q1}$, —$NR^{Q1}{}_2$, —$NR^{Q2}R^{Q3}$, —C(=O)—$NH_2$, —C(=O)—$NHR^{Q1}$, —C(=O)—$NR^{Q1}{}_2$, —C(=O)—$NR^{Q2}R^{Q3}$, phenyl, or benzyl; wherein each $R^{Q1}$ is independently $C_{1-4}$alkyl, phenyl, or benzyl; and each —$NR^{Q2}R^{Q3}$ is independently pyrrolidino, piperidino, piperizino, or morpholino, and is independently unsubstituted or substituted with one or more groups selected from $C_{1-3}$alkyl and —$CF_3$.

In one embodiment, each —$R^{G3}$, if present, is independently —F, —Cl, —Br, —I, —OH, —OMe, —OEt, or —$OCF_3$.

Some Preferred Combinations

Each and every compatible combination of the embodiments described above is explicitly disclosed herein, as if each and every combination was individually and explicitly recited.

In this respect, the skilled person will readily recognize any combination of embodiments (e.g., combination of substituents) that may be, or are, chemically unstable. The skilled person would either avoid such combinations, or employ suitable synthetic strategies (e.g., well known protecting groups).

In one embodiment:
-A is independently phenyl;
-$Q^1$- is independently a covalent bond;
—$R^N$ is independently —H or aliphatic $C_{1-4}$alkyl; and
—$R^B$— is independently —CH=CH—.

In one embodiment:
-A is independently phenyl;
-$Q^1$- is independently a covalent bond;
—$R^N$ is independently —H or -Me; and
—$R^B$— is independently —CH=CH—.

In one embodiment:
-A is independently phenyl;
-$Q^1$- is independently a covalent bond;
—$R^N$ is independently —H; and
—$R^B$— is independently —CH=CH—;
for example, as in the following compound (PXD101):

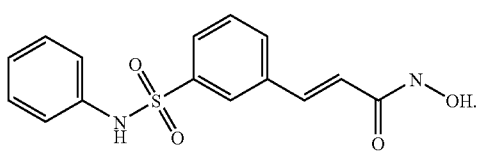 [SMILES: O=C(/C=C/c1cccc(S(=O)(=O)Nc2ccccc2)c1)NO]

Salts, Solvates, and Hydrates

It may be convenient or desirable to prepare; purify, and/or handle a corresponding salt of a target compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

It may be convenient or desirable to prepare, purify, and/or handle a corresponding solvate of a target compound. The term "solvate" is used herein in the conventional sense to refer to a complex of solute (e.g., compound, salt of compound) and solvent. If the solvent is water, the solvate may be conveniently referred to as a hydrate, for example, a monohydrate, a di-hydrate, a tri-hydrate, etc.

Unless otherwise specified, a reference to a particular compound also includes solvate and hydrate forms thereof.

Methods of Chemical Synthesis

In one embodiment, the method comprises the steps of, in order:
(AAA) alkenyl-acid addition, comprising:
  either (i): the steps of, in order:
    (ACAEA) alkenyl-carboxylic acid ester addition;
    ($PUR^E$) optional purification; and
    (CAD) carboxylic acid deprotection;
  or (ii): the step of:
    (ACAA) alkenyl-carboxylic acid addition;
($PUR^F$) optional purification;
(HAF) hydroxamic acid formation; and
($PUR^G$) optional purification.

In one embodiment, the method comprises the steps of, in order:
(AAA) alkenyl-acid addition, comprising the steps of, in order:
  (ACAEA) alkenyl-carboxylic acid ester addition;
  ($PUR^E$) optional purification; and
  (CAD) carboxylic acid deprotection;
($PUR^F$) optional purification;
(HAF) hydroxamic acid formation; and
($PUR^G$) optional purification.

In one embodiment, the method comprises the steps of, in order:
(SAF) sulfonamide formation;
($PUR^C$) optional purification;

(AAA) alkenyl-acid addition, comprising:
  either (i): the steps of, in order:
    (ACAEA) alkenyl-carboxylic acid ester addition;
    (PUR$^E$) optional purification; and
    (CAD) carboxylic acid deprotection;
  or (ii): the step of:
    (ACAA) alkenyl-carboxylic acid addition;
(PUR$^F$) optional purification;
(HAF) hydroxamic acid formation; and
(PUR$^G$) optional purification.

In one embodiment, the method comprises the steps of, in order:

(SAF) sulfonamide formation;
(PUR$^C$) optional purification;
(AAA) alkenyl-acid addition, comprising the steps of, in order:
  (ACAEA) alkenyl-carboxylic acid ester addition;
  (PUR$^E$) optional purification; and
  (CAD) carboxylic acid deprotection;
(PUR$^F$) optional purification;
(HAF) hydroxamic acid formation; and
(PUR$^G$) optional purification.

In one embodiment, the method is as illustrated in the following scheme.

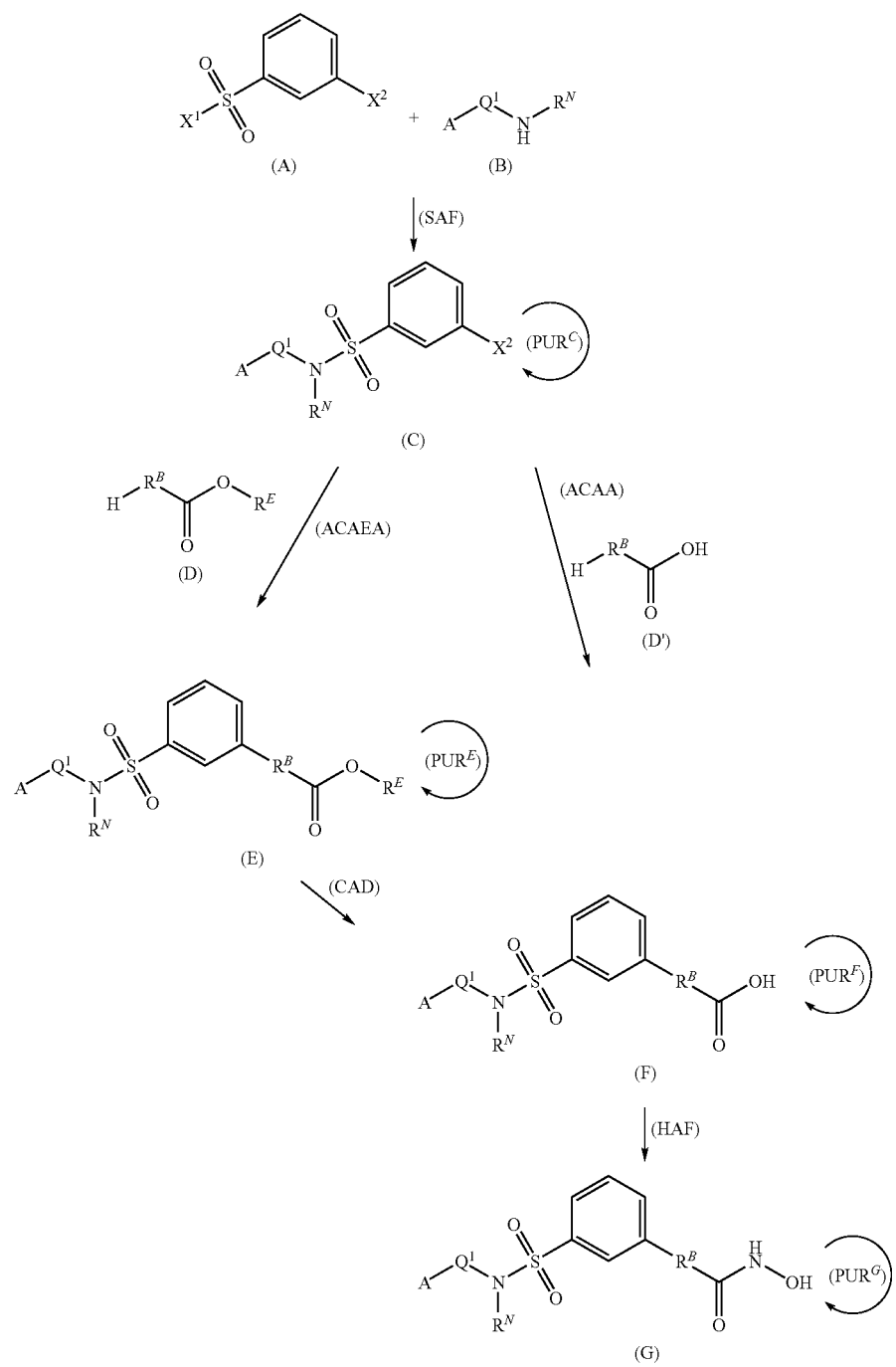

Scheme 2

In one embodiment, the method is as illustrated in the following scheme.
Scheme 3
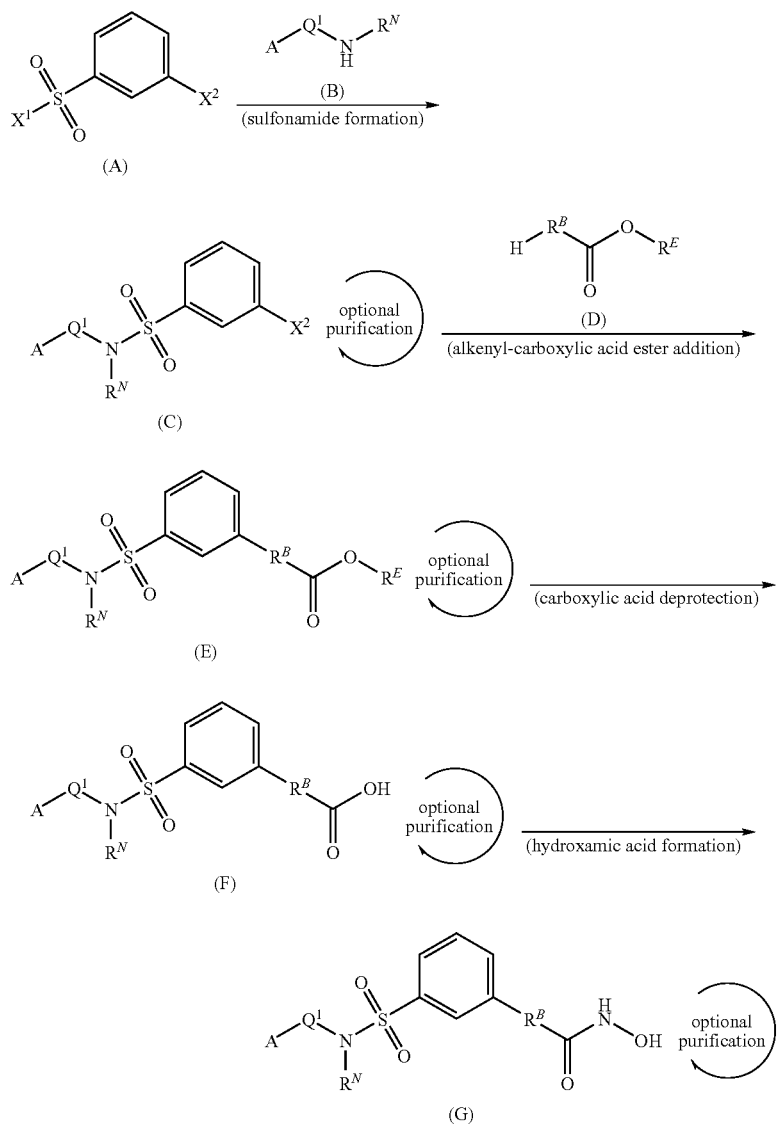
In an especially preferred embodiment, the method is illustrated in the following scheme, wherein the compound of Formula (1) is an example of a compound of Formula (A) above, the compound of Formula (2) is an example of a compound of Formula (B) above, etc.
Scheme 4
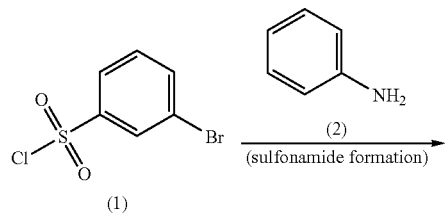

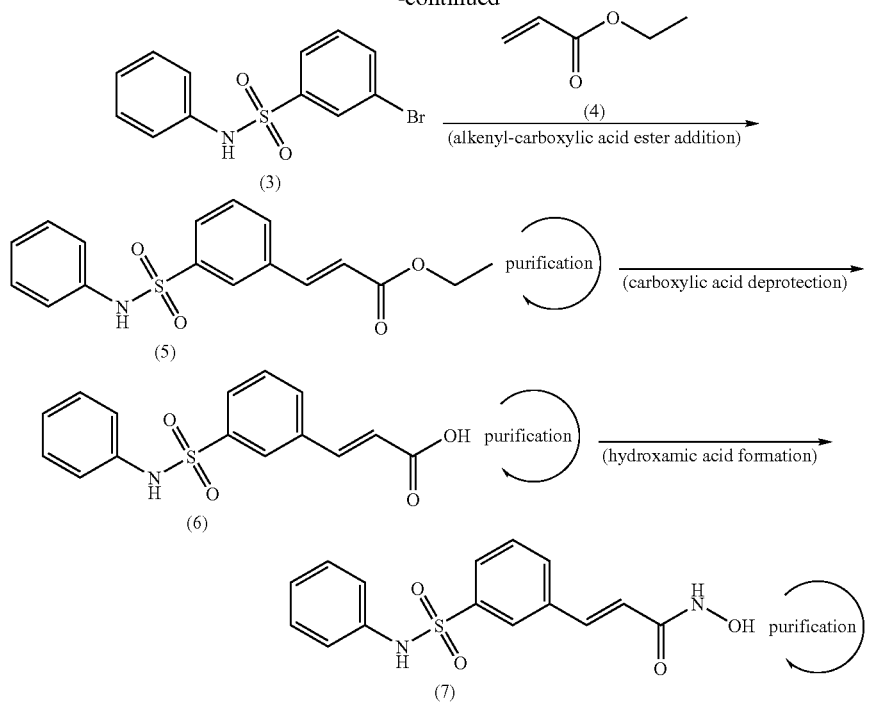

Sulfonamide Formation (SAF)

In this step, a meta-halo-phenyl-halosulfonyl compound (A) is converted to a meta-halo-phenyl-sulfonamide compound (C) by reaction with an amine (B), as in, for example:

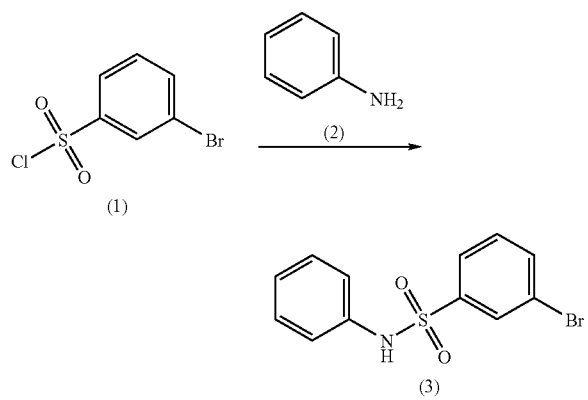

In one embodiment, the (SAF) step comprises the step of:
(SAF-1) reacting a compound of Formula (A) with a compound of Formula (B) under conditions suitable to form a compound of Formula (C):

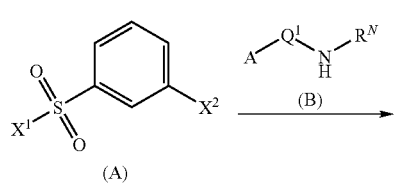

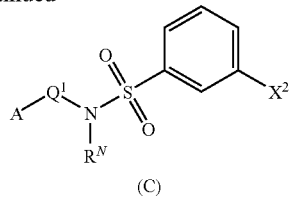

wherein:
—$X^1$ is independently —Cl, —Br, or —I;
—$X^2$ is independently —Cl, —Br, or —I; and
-A, -$Q^1$-, and —$R^N$ are as defined herein.

In one embodiment, —$X^1$ is independently —Cl, —Br, or —I.
In one embodiment, —$X^1$ is independently —Cl.
In one embodiment, —$X^1$ is independently —Br.
In one embodiment, —$X^1$ is independently —I.
In one embodiment, —$X^2$ is independently —Cl, —Br, or —I.
In one embodiment, —$X^2$ is independently —Cl.
In one embodiment, —$X^2$ is independently —Br.
In one embodiment, —$X^2$ is independently —I.
In one embodiment, —$X^1$ and —$X^2$ are the same.
In one embodiment, —$X^1$ and —$X^2$ are different.
In one embodiment, —$X^1$ is —Cl and —$X^2$ is —Br.
In one embodiment, the compound of Formula (B) is aniline:

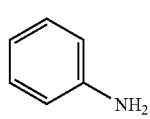

In one embodiment, the reaction of step (SAF-1) is performed in an organic solvent.

In one embodiment, the reaction of step (SAF-1) is performed in an organic solvent comprising toluene.

In one embodiment, the reaction of step (SAF-1) is performed in the presence of a base.

In one embodiment, the reaction of step (SAF-1) is performed in the presence of an organic base.

In one embodiment, the reaction of step (SAF-1) is performed in the presence of DMAP.

In one embodiment, the reaction of step (SAF-1) is performed at a temperature of 40-70° C. In one embodiment, the temperature is 50-60° C.

In one embodiment, in the reaction of step (SAF-1), the compound of Formula (B) is added to the reaction mixture over a period of 10 to 180 minutes.

In one embodiment, the period is 10 to 60 minutes.

In one embodiment, the period is about 30 minutes.

In one embodiment, in the reaction of step (SAF-1), the molar ratio of the compound Formula (A) to the compound of Formula (B) is 0.1 to 1. In one embodiment, the molar ratio is 0.3 to 0.6. In one embodiment, the molar ratio is about 0.45.

In one embodiment, the reaction of step (SAF-1) is followed by the additional step of:
(SAF-2) quenching the reaction mixture produced in step (SAF-1) with acid.

In one embodiment, the acid used in step (SAF-2) is aqueous acid.

In one embodiment, the acid used in step (SAF-2) is HCl.

In one embodiment, the acid used in step (SAF-2) is aqueous HCl.

In one embodiment, the reaction of step (SAF-1) is performed in an organic solvent, and is followed by the additional steps, in order, of:
(SAF-2) quenching the reaction mixture produced in step (SAF-1) with acid, wherein the acid in step (SAF-2) is aqueous acid;
(SAF-3) separating the reaction mixture produced in step (SAF-2) to provide an organic fraction; and
(SAF-4) treating the organic fraction produced in step (SAF-3) with base.

In one embodiment, the base used in step (SAF-4) is aqueous base.

In one embodiment, the base used in step (SAF-4) is bicarbonate.

In one embodiment, the base used in step (SAF-4) is sodium bicarbonate.

In one embodiment, the base used in step (SAF-4) is 5% (w/w) aqueous sodium bicarbonate.

In one embodiment, the reaction of step (SAF-4) is performed at a temperature of 35-65° C. In one embodiment, the temperature is 45-55° C.

Optional Purification (PUR$^C$)

In this optional step, a meta-halo-phenyl-sulfonamide compound (C) is purified.

In one embodiment, the step comprises:
(PUR$^C$) optionally purifying a compound of Formula (C), as defined herein.

In one embodiment, this optional step is included (i.e., is performed; is not optional).

In one embodiment, this optional step is omitted.

In one embodiment, the step (PUR$^C$) comprises one or more steps selected from:
a step of purifying a compound of Formula (C) by filtration;
a step of purifying a compound of Formula (C) by precipitation; and
a step of purifying a compound of Formula (C) by recrystallisation.

Alkenyl-Acid Addition (AAA)

The alkenyl-acid addition (AAA) step comprises:
either: the steps of, in order:
(ACAEA) alkenyl-carboxylic acid ester addition;
(PUR$^E$) optional purification; and
(CAD) carboxylic acid deprotection;
or: the step of:
(ACAA) alkenyl-carboxylic acid addition.

In this step:

either (i):
a meta-halo-phenyl-sulfonamide compound (C) is converted to a meta-alkenyl-carboxylic acid ester-phenyl-sulfonamide compound (E) by reaction with an alkenyl-carboxylic acid ester (D), as in, for example:

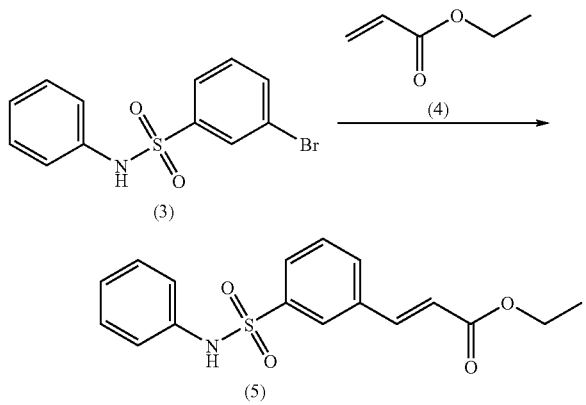

optionally, the meta-alkenyl-carboxylic acid ester-phenyl-sulfonamide compound (E) is purified; and the meta-alkenyl-carboxylic acid ester-phenyl-sulfonamide compound (E) is de-esterified to give a meta-alkenyl-carboxylic acid-phenyl-sulfonamide compound (F), as in, for example:

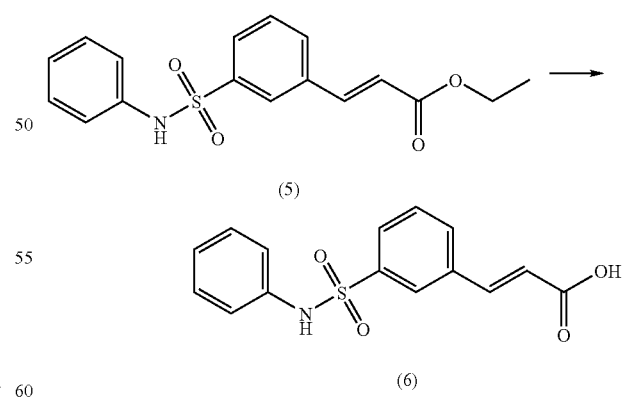

or (ii):
a meta-halo-phenyl-sulfonamide compound (C) is converted to a meta-alkenyl-carboxylic acid-phenyl-sulfonamide compound (F) by reaction with an alkenyl-carboxylic acid (D'), as in, for example:

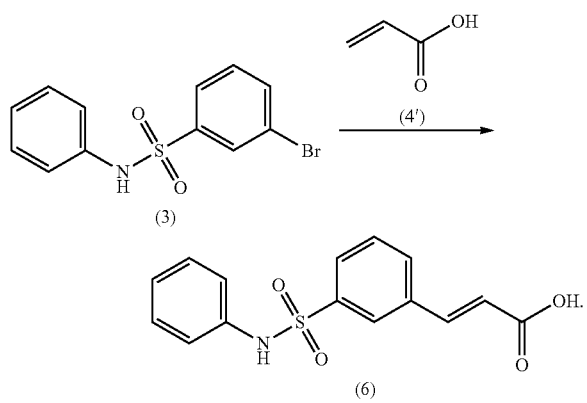

(3)

(4')

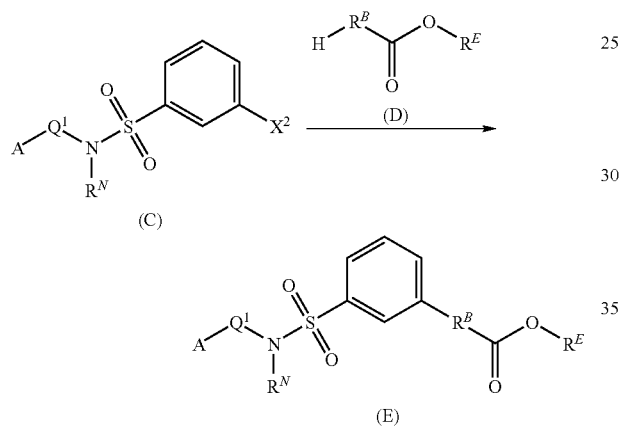

(6)

In one embodiment, the (AAA) step comprises:
either (i): the steps of, in order:
(ACAEA-1) reacting a compound of Formula (C) with a compound of Formula (D) under conditions suitable to form a compound of Formula (E):

(C)

(D)

(E)

(PUR$^E$) optional purifying the compound of Formula (E); and
(CAD-1) reacting the compound of Formula (E) under conditions suitable to form a compound of Formula (F):

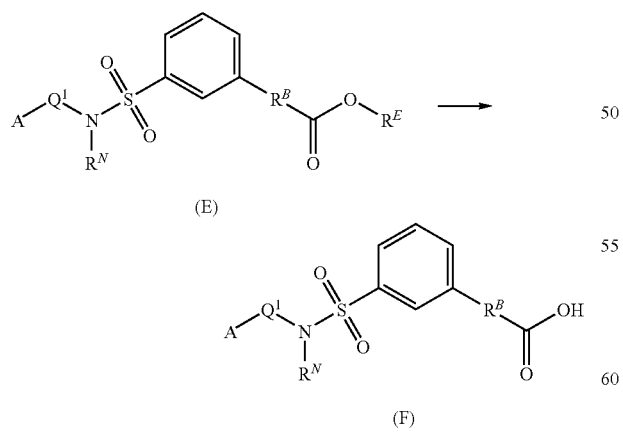

(E)

(F)

or (ii): the step of:
(ACAA-1) reacting a compound of Formula (C) with a compound of Formula (D') under conditions suitable to form a compound of Formula (F):

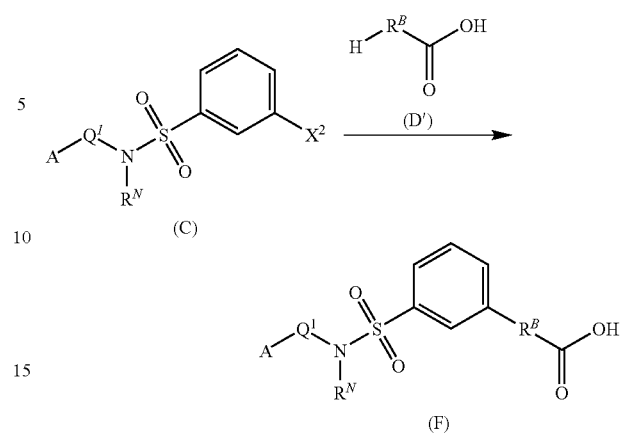

(C)

(D')

(F)

wherein:
—$R^E$ is a carboxylic acid-protecting ester group; and
-A, -Q$^1$-, —R$^N$, —X$^2$, and —R$^B$— are as defined herein.

In one embodiment, the (AAA) step comprises the steps of, in order:
(ACAEA-1) reacting a compound of Formula (C) with a compound of Formula (D) under conditions suitable to form a compound of Formula (E):

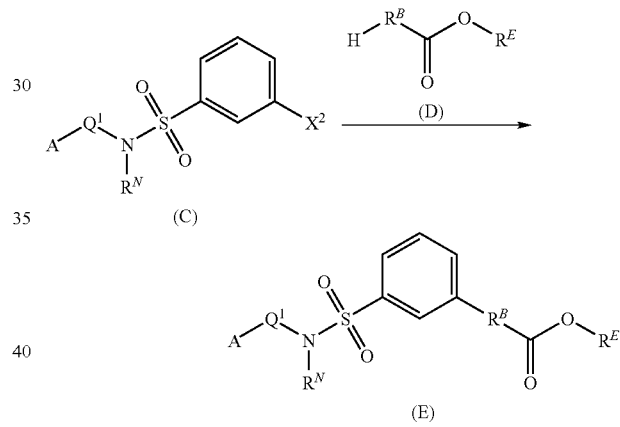

(C)

(D)

(E)

(PUR$^E$) optional purifying the compound of Formula (E); and
(CAD-1) reacting the compound of Formula (E) under conditions suitable to form a compound of Formula (F):

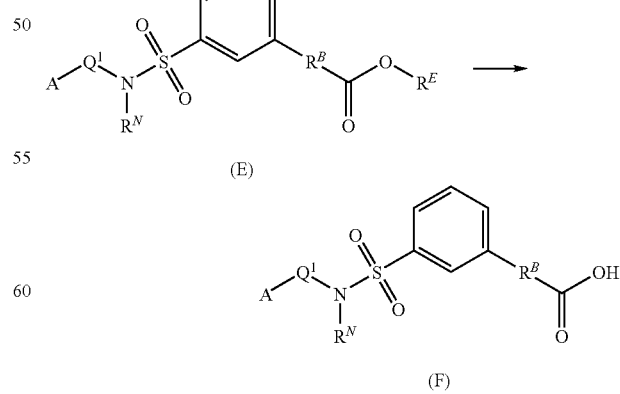

(E)

(F)

wherein:
—$R^E$ is a carboxylic acid-protecting ester group; and
-A, -Q$^1$-, —R$^N$, —X$^2$, and —R$^B$— are as defined herein.

Alkenyl-Carboxylic Acid Ester Addition (ACAEA-1)

In this step, a meta-halo-phenyl-sulfonamide compound (C) is converted to a meta-alkenyl-carboxylic acid ester-phenyl-sulfonamide compound (E) by reaction with an alkenyl-carboxylic acid ester (D), as in, for example:

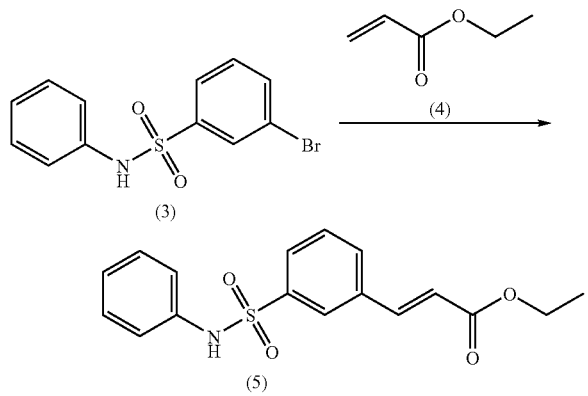

In one embodiment, the step comprises:
(ACAEA-1) reacting a compound of Formula (C) with a compound of Formula (D) under conditions suitable to form a compound of Formula (E):

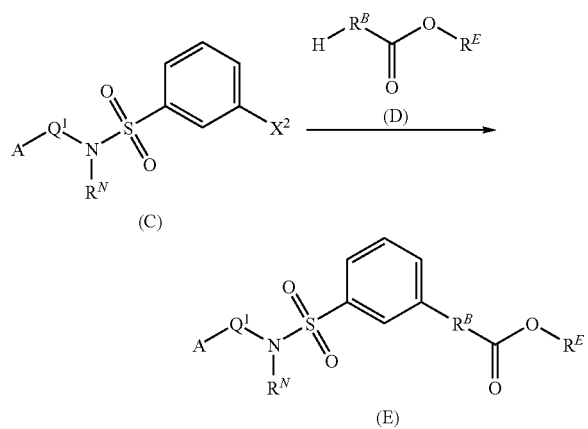

wherein:
—$R^E$ is a carboxylic acid-protecting ester group; and
-A, -$Q^1$-, —$R^N$, —$X^2$, and —$R^B$— are as defined herein.

In one embodiment, the reaction of step (ACAEA-1) is performed in an organic solvent.

In one embodiment, the reaction of step (ACAEA-1) is performed in an organic solvent comprising toluene.

In one embodiment, the reaction of step (ACAEA-1) is performed at a temperature of 70-110° C. In one embodiment, the temperature is 80-90° C.

In one embodiment, in the reaction of step (ACAEA-1), the compound of Formula (D) is added to the reaction mixture of step (ACAEA-1) over a period of 10 to 400 minutes. In one embodiment, the period is 30 to 300 minutes. In one embodiment, the period is about 165 minutes.

In one embodiment, in the reaction of step (ACAEA-1), the molar ratio of the compound Formula (C) to the compound of Formula (D) is 0.5 to 2. In one embodiment, the molar ratio is 0.8 to 1.2.

Catalyst:
In one embodiment, the reaction of step (ACAEA-1) is performed in the presence of a catalyst.

In one embodiment, the catalyst is a palladium catalyst.
In one embodiment, the catalyst is a palladium (0) catalyst.
In one embodiment, the palladium (0) catalyst is added to the reaction mixture of step (ACAEA-1), prior to the addition of the compound of Formula (D).

In one embodiment, the palladium (0) catalyst is prepared in situ, in the reaction mixture of step (ACAEA-1), prior to the addition of the compound of Formula (D).

In one embodiment, the palladium (0) catalyst is prepared by reaction of a palladium (II) compound, e.g., under conditions suitable to form said palladium (0) catalyst.

For example, the palladium (0) catalyst may be "ligand free" or "homeopathic ligand-free" palladium (0), as is well known in the art. Alternatively, the palladium (0) catalyst may be stabilized using one or more ligands, for example, phosphines or phosphites, as is also well known in the art.

In one embodiment, the palladium (0) catalyst is prepared by reaction of a palladium (II) compound and a phosphine or a phosphite, e.g., under conditions suitable to form said palladium (0) catalyst.

In one embodiment, the palladium (0) catalyst is prepared by reaction of a palladium (II) compound and a phosphine, e.g., under conditions suitable to form said palladium (0) catalyst.

In one embodiment, the palladium (0) catalyst is prepared by reaction of a palladium (II) compound, a phosphine or a phosphite, and a base (for convenience, referred to as an "assisting base"), e.g., under conditions suitable to form said palladium (0) catalyst.

In one embodiment, the palladium (0) catalyst is prepared by reaction of a palladium (II) compound, a phosphine, and a base (for convenience, referred to as an "assisting base"), e.g., under conditions suitable to form said palladium (0) catalyst.

In one embodiment, the palladium (0) catalyst is prepared in situ, in the reaction mixture of step (ACAEA-1), by reaction of a palladium (II) compound and a phosphine or a phosphite, e.g., under conditions suitable to form said palladium (0) catalyst.

In one embodiment, the palladium (0) catalyst is prepared in situ, in the reaction mixture of step (ACAEA-1), by reaction of a palladium (II) compound and a phosphine, e.g., under conditions suitable to form said palladium (0) catalyst.

In one embodiment, the palladium (0) catalyst is prepared in situ, in the reaction mixture of step (ACAEA-1), by reaction of a palladium (II) compound, a phosphine or a phosphite, and a base (again, for convenience, referred to as an "assisting base"), e.g., under conditions suitable to form said palladium (0) catalyst.

In one embodiment, the palladium (0) catalyst is prepared in situ, in the reaction mixture of step (ACAEA-1), by reaction of a palladium (II) compound, a phosphine, and a base (again, for convenience, referred to as an "assisting base"), e.g., under conditions suitable to form said palladium (0) catalyst.

In one embodiment, the step (ACAEA-1) comprises:
(ACAEA-1a) adding a palladium (II) compound and a phosphine to a reaction mixture comprising the compound of Formula (C) under conditions suitable to form a palladium (0) catalyst; and subsequently
(ACAEA-1b) adding the compound of Formula (D) under conditions suitable to form a compound of Formula (E).

In one embodiment, the step (ACAEA-11) comprises:
(ACAEA-1aa) adding a palladium (II) compound, a phosphine, and a base (again, for convenience, referred to as an "assisting base") to a reaction mixture comprising the compound of Formula (C) under conditions suitable to form a palladium (0) catalyst; and subsequently (ACAEA-1b) adding to the reaction mixture produced in step (ACAEA-1aa) the compound of Formula (D) under conditions suitable to form a compound of Formula (E).

In one embodiment, the palladium (II) compound is palladium (II) acetate.

Examples of suitable phosphines include the following:

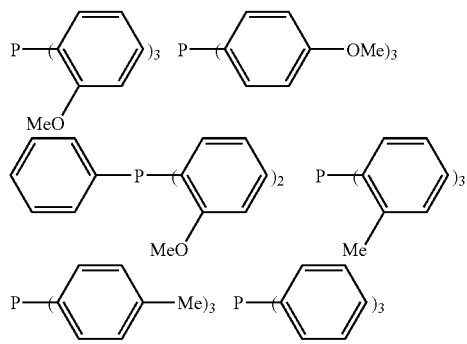

In one embodiment, the phosphine is a triarylphosphine.

In one embodiment, the phosphine is triphenylphosphine or tri(tolyl)phosphine.

In one embodiment, the phosphine is tri(o-tolyl)phosphine.

Examples of suitable phosphites include the following:

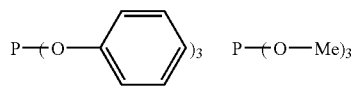

In one embodiment, the base (i.e., the assisting base) is an organic base.

In one embodiment, the base (i.e., the assisting base) is tri($C_{1-4}$alkyl)amine.

In one embodiment, the base (i.e., the assisting base) is triethylamine or tributylamine.

In one embodiment, the base (i.e., the assisting base) is triethylamine.

In one embodiment, the base (i.e., the assisting base) is tributylamine.

In one embodiment, the reaction to form said palladium (0) catalyst (e.g., the reaction of step (ACAEA-1a) or (ACAEA-1aa)) is performed at a temperature of 35-65° C. In one embodiment, the temperature is 45-55° C.

In one embodiment, the reaction to form said palladium (0) catalyst (e.g., the reaction of step (ACAEA-1a) or (ACAEA-1aa)) further comprises degassing the reaction mixture after formation of the palladium (0) catalyst.

The Ester Group:

In one embodiment, —$R^E$ is a carboxylic acid-protecting ester group.

In this respect, —$R^E$ is any suitable carboxylic acid-protecting ester group that is compatible with the reaction(s) in the step (ACAEA-1).

In one embodiment, —$R^E$ is independently:
—$R^{S1}$, —$R^{S2}$, —$R^{S3}$, —$R^{S4}$, —$R^{S5}$, —$R^{S6}$, —$R^{S7}$, —$R^{S8}$, -$L^S$-$R^{S4}$, -$L^S$-$R^{S5}$, -$L^S$-$R^{S6}$, -$L^S$-$R^{S7}$, or -$L^S$-$R^{S8}$,
wherein:
each —$R^{S1}$ is independently saturated aliphatic $C_{1-6}$alkyl;
each —$R^{S2}$ is independently aliphatic $C_{2-6}$alkenyl;
each —$R^{S3}$ is independently aliphatic $C_{2-6}$alkynyl;
each —$R^{S4}$ is independently saturated $C_{3-6}$cycloalkyl;
each —$R^{S5}$ is independently $C_{3-6}$cycloalkenyl;
each —$R^{S6}$ is independently non-aromatic $C_{3-7}$heterocyclyl;
each —$R^{S7}$ is independently $C_{6-14}$carboaryl;
each —$R^{S8}$ is independently $C_{5-14}$heteroaryl;
each -$L^S$- is independently saturated aliphatic $C_{1-3}$alkylene;
and wherein:
each $C_{1-6}$alkyl, $C_{2-6}$alkenyl, $C_{2-6}$alkynyl, $C_{3-6}$cycloalkyl, $C_{3-6}$cycloalkenyl, non-aromatic $C_{3-7}$heterocyclyl, $C_{6-14}$carboaryl, $C_{5-14}$heteroaryl, and $C_{1-3}$alkylene is optionally substituted, for example, with one or more (e.g., 1, 2, 3) substituents —$R^{S9}$, wherein each —$R^{S9}$ is independently:
—F, —Cl, —Br, —I,
—$R^{T1}$,
—$CF_3$, —$CH_2CF_3$, —$CF_2CF_2H$, —$OCF_3$, —$OCH_2CF_3$, —$OCF_2CF_2H$,
—OH, -$L^T$-OH, —O-$L^T$-OH,
—$OR^{T1}$, -$L^T$-$OR^{T1}$, —O-$L^T$-$OR^{T1}$,
—CN,
—$NO_2$,
—$NH_2$, —$NHR^{T1}$, —$NR^{T1}_2$, —$NR^{T2}R^{T3}$,
-$L^T$-$NH_2$, -$L^T$-$NHR^{T1}$, -$L^T$-$NR^{T1}_2$, or -$L^T$-$NR^{T2}R^{T3}$,
—O-$L^T$-$NH_2$, —O-$L^T$-$NHR^{T1}$, —O-$L^T$-$NR^{T1}_2$, —O-$L^T$-$NR^{T2}R^{T3}$,
—NH-$L^T$-$NH_2$, —NH-$L^T$-$NHR^{T1}$, —NH-$L^T$-$NR^{T1}_2$, —NH-$L^T$-$NR^{T2}R^{T3}$,
—$NR^{T1}$-$L^T$-$NH_2$, —$NR^{T1}$-$L^T$-$NHR^{T1}$, —$NR^{T1}$-$L^T$-$NR^{T1}_2$, —$NR^{T1}$-$L^T$-$NR^{T2}R^{T3}$,
—C(=O)OH, —C(=O)$OR^{T1}$,
—C(=O)$NH_2$, —C(=O)$NHR^{T1}$, —C(=O)$NR^{T1}_2$, or —C(=O)$NR^{T2}R^{T3}$;
wherein:
each —$R^{T1}$ is independently saturated aliphatic $C_{1-4}$alkyl, phenyl, or benzyl;
each -$L^T$- is independently saturated aliphatic $C_{1-5}$alkylene; and
in each group —$NR^{T2}R^{T3}$, —$R^{T2}$ and —$R^{T3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteratoms is independently N, O, or S.

In one embodiment, —$R^E$ is independently:
—$R^{S1}$, —$R^{S4}$, —$R^{S7}$, —$R^{S8}$
-$L^S$-$R^{S4}$, -$L^S$-$R^{S7}$, or -$L^S R^{S8}$.

In one embodiment, —$R^E$ is independently —$R^{S1}$, —$R^{S4}$, —$R^{S7}$, -$L^S$-$R^{S4}$, or -$L^S$-$R^{S7}$.

In one embodiment, —$R^E$ is independently —$R^{S1}$, —$R^{S7}$, or -$L^S$-$R^{S7}$.

In one embodiment, —$R^E$ is independently —$R^{S1}$.

In one embodiment, each —$R^{S7}$, if present, is independently phenyl or naphthyl; and is optionally substituted.

In one embodiment, each —$R^{S7}$, if present, is independently phenyl; and is optionally substituted.

In one embodiment, each —$R^{S8}$, if present, is independently furanyl, thienyl, pyrrolyl, imidazolyl, pyrazolyl, triazolyl, oxazolyl, isoxazoly, thiazolyl, isothiazolyl, pyridyl, pyrazinyl, pyrimidinyl, pyridazinyl, benzofuranyl, isobenzofuranyl, indazolyl, purinyl, quinolinyl, isoquinolinyl, naphthyridinyl, quinoxalinyl, quinazolinyl, cinnolinyl, indoly, isoindolyl, carbazolyl, carbolinyl, acridinyl, phenoxazinyl, or phenothiazinyl; and is optionally substituted.

In one embodiment, each —$R^{S8}$, if present, is independently $C_{5-6}$heteroaryl; and is optionally substituted.

In one embodiment, each —R$^{S8}$, if present, is independently furanyl, thienyl, pyrrolyl, imidazolyl, pyrazolyl, triazolyl, oxazolyl, isoxazoly, thiazolyl, isothiazolyl, pyridyl, pyrazinyl, pyrimidinyl, or pyridazinyl; and is optionally substituted.

In one embodiment, each —R$^{S8}$, if present, is independently furanyl, pyrrolyl, pyrazolyl, triazolyl, oxazolyl, isoxazoly, thiazolyl, isothiazolyl, or pyridyl; and is optionally substituted.

In one embodiment, each -L$^S$-, if present, is independently —CH$_2$—.

In one embodiment, each —R$^{T1}$ is independently saturated aliphatic C$_{1-4}$alkyl.

In one embodiment, each group —NR$^{T2}$R$^{T3}$, if present, is independently pyrrolidino, imidazolidino, pyrazolidino, piperidino, piperizino, morpholino, thiomorpholino, azepino, or diazepino, and is independently unsubstituted or substituted, for example, with one or more (e.g., 1, 2, 3) groups selected from C$_{1-3}$alkyl and —CF$_3$.

In one embodiment, each group —NR$^{T2}$R$^{T3}$, if present, is independently pyrrolidino, piperidino, piperizino, or morpholino, and is independently unsubstituted or substituted, for example, with one or more (e.g., 1, 2, 3) groups selected from C$_{1-3}$alkyl and —CF$_3$.

In one embodiment, each —R$^{S9}$, if present, is independently —F, —Cl, —Br, —I, —OH, —OMe, —OEt, or —OCF$_3$.

In one embodiment, —R$^E$ is independently -Me, -Et, -nPr, -iPr, -nBu, -iBu, -sBu, -tBu, -Ph, or —CH$_2$-Ph.

In one embodiment, —R$^E$ is independently -Me, -Et, -nPr, -iPr, -nBu, -iBu, -sBu, or -tBu.

In one embodiment, —R$^E$ is independently -Et.

In one embodiment, the compound of Formula (D) is acrylic acid ethyl ester:

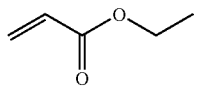

Optional Purification (PUR$^E$)

In this optional step, a meta-alkenyl-carboxylic acid ester-phenyl-sulfonamide compound (E) is purified.

In one embodiment, the step comprises:
(PUR$^E$) optionally purifying a compound of Formula (E), as defined herein.

In one embodiment, this optional step is included (i.e., is performed; is not optional).

In one embodiment, this optional step is omitted.

In one embodiment, the step (PUR$^E$) comprises one or more steps selected from:
a step of purifying a compound of Formula (E) by filtration;
a step of purifying a compound of Formula (E) by precipitation;
a step of purifying a compound of Formula (E) by treatment with carbon; and
a step of purifying a compound of Formula (E) by recrystallisation.

In one embodiment, the step (PUR$^E$) comprises (or further comprises) a step of purifying a compound of Formula (E) by filtration.

In one embodiment, the step (PUR$^E$) comprises (or further comprises) a step of purifying a compound of Formula (E) by precipitation.

In one embodiment, the step (PUR$^E$) comprises (or further comprises) a step of purifying a compound of Formula (E) by treatment with carbon.

In one embodiment, the step (PUR$^E$) comprises (or further comprises) a step of purifying a compound of Formula (E) by treatment with recrystallisation.

For example, in one embodiment, the step (PUR$^E$) comprises the following steps, in order:
a step of purifying a compound of Formula (E) by filtration;
a first step of purifying a compound of Formula (E) by precipitation;
a step of purifying a compound of Formula (E) by treatment with carbon; and
a second step of purifying a compound of Formula (E) by precipitation.

Purification by Filtration:

In one embodiment, the purification by filtration is filtering a mixture of the compound of Formula (E) and a filtration solvent, and collecting the filtrate.

In one embodiment, the purification by filtration is by forming a mixture of the compound of Formula (E) with a filtration solvent, filtering the mixture, and collecting the filtrate.

In one embodiment, the filtration solvent comprises an organic solvent. In one embodiment, the filtration solvent comprises ethyl acetate.

In one embodiment, the filtration is performed at a temperature of 35-65° C.

In one embodiment, the filtration is performed at a temperature of 45-55° C.

Purification by Precipitation:

In one embodiment, the purification by precipitation is by cooling a liquid mixture comprising dissolved compound of Formula (E) to form a precipitate comprising the compound of Formula (E), and collecting the precipitate (e.g., by filtration).

In one embodiment, the purification by precipitation is by cooling a liquid mixture comprising dissolved compound of Formula (E) to form a precipitate comprising the compound of Formula (E), collecting the precipitate (e.g., by filtration), and washing the collected precipitate (e.g., with heptanes).

In one embodiment, the purification by precipitation is by cooling a liquid mixture comprising dissolved compound of Formula (E) to form a precipitate comprising the compound of Formula (E), collecting the precipitate (e.g., by filtration), and drying the collected precipitate (e.g., in an oven).

In one embodiment, the purification by precipitation is by cooling a liquid mixture comprising dissolved compound of Formula (E) to form a precipitate comprising the compound of Formula (E), collecting the precipitate (e.g., by filtration), washing the collected precipitate (e.g., with heptanes), and drying the washed precipitate (e.g., in an oven).

In one embodiment, the cooling is to a temperature of 0-20° C.

In one embodiment, the cooling is to a temperature of 0-10° C.

In one embodiment, the cooling is for a time of 10 minutes to 7 days.

In one embodiment, the cooling is for a time of about 1 hour.

In one embodiment, the cooling is for a time of about 1 day.

In one embodiment, the drying is at a temperature of 35-65° C.

In one embodiment, the drying is at a temperature of 45-55° C.

In one embodiment, the drying is for a time of 1 hour to 7 days.

In one embodiment, the drying is for a time of about 1 day.
In one embodiment, the drying is under vacuum.
Purification by Treatment with Carbon:
In one embodiment, the purification by treatment with carbon is by treating a liquid mixture comprising dissolved compound of Formula (E) with carbon.

In one embodiment, the carbon comprises activated carbon.

In one embodiment, the liquid mixture comprising dissolved compound of Formula (E) further comprises an organic solvent. In one embodiment, the organic solvent comprises ethyl acetate. In one embodiment, the organic solvent is ethyl acetate.

In one embodiment, the treatment with carbon is performed at a temperature of 30-60° C.

In one embodiment, the temperature is 40-50° C.

In one embodiment, the treatment with carbon is performed for a time of 10 minutes to 1 day.

In one embodiment, the treatment with carbon is performed for a time of about 3 hours.

Purification by Recrystallisation:

In one embodiment, the recrystallisation is by dissolving the compound of Formula (E) in a recrystallisation solvent, cooling the resulting solution to form a precipitate comprising the compound of Formula (E), and collecting the precipitate (e.g., by filtration).

In one embodiment, the recrystallisation is by dissolving the compound of Formula (E) in a recrystallisation solvent, cooling the resulting solution to form a precipitate comprising the compound of Formula (E), collecting the precipitate (e.g., by filtration), and washing the collected precipitate (e.g., with recrystallisation solvent).

In one embodiment, the recrystallisation is by dissolving the compound of Formula (E) in a recrystallisation solvent, cooling the resulting solution to form a precipitate comprising the compound of Formula (E), collecting the precipitate (e.g., by filtration), washing the collected precipitate (e.g., with recrystallisation solvent), and drying the washed precipitate (e.g., in an oven).

In one embodiment, the recrystallisation is by dissolving the compound of Formula (E) in a recrystallisation solvent, cooling the resulting solution to form a precipitate comprising the compound of Formula (E), collecting the precipitate (e.g., by filtration), and drying the collected precipitate (e.g., in an oven).

In one embodiment, the step of dissolving the compound of Formula (E) in a recrystallisation solvent includes the step of heating a mixture of the compound of
Formula (E) and the recrystallisation solvent, before the step of cooling the resulting solution to form a precipitate comprising the compound of Formula (E).

In one embodiment, the recrystallisation solvent is an organic solvent.

In one embodiment, the recrystallisation solvent is acetonitrile.

In one embodiment, the heating is heating to reflux.

In one embodiment, the heating is heating to about 80° C.

In one embodiment, the heating is for a time of 10 minutes to 6 hours.

In one embodiment, the heating is for a time of about 2 hours.

In one embodiment, the cooling is to a temperature of 0-20° C.

In one embodiment, the cooling is to a temperature of 0-10° C.

In one embodiment, the cooling is for a time of 10 minutes to 12 hours.

In one embodiment, the cooling is for a time of about 6 hours.

In one embodiment, the drying is at a temperature of 35-65° C.

In one embodiment, the drying is at a temperature of 45-55° C.

In one embodiment, the drying is for a time of 1 hour to 7 days.

In one embodiment, the drying is for a time of about 1 day.

Carboxylic Acid Deprotection (CAD)

In this step, a meta-alkenyl-carboxylic acid ester-phenyl-sulfonamide compound (E) is de-esterified to give a meta-alkenyl-carboxylic acid-phenyl-sulfonamide compound (F), as in, for example:

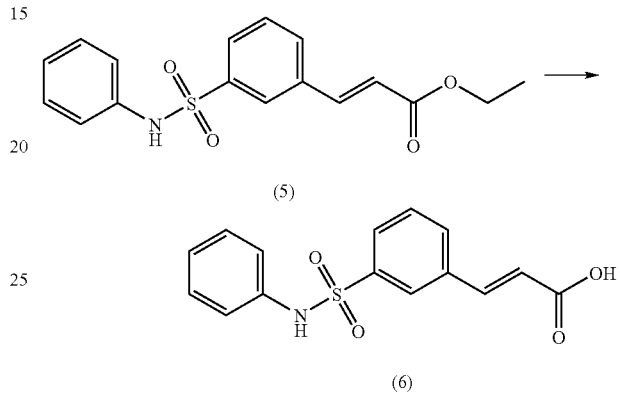

(5)

(6)

In one embodiment, the step comprises:
(CAD-1) reacting a compound of Formula (E) under conditions suitable to form a compound of Formula (F):

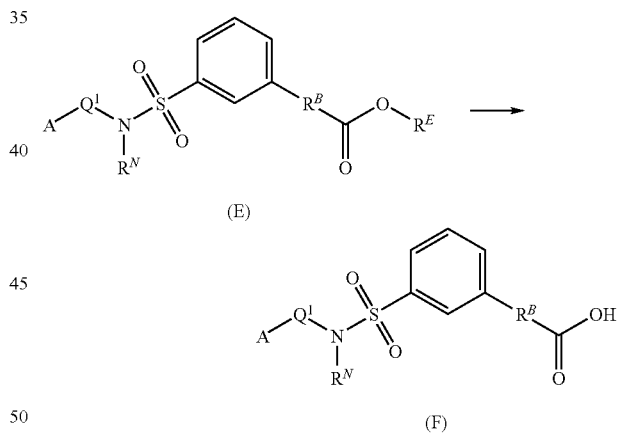

(E)

(F)

wherein:
-A, -Q¹-, —R$^N$, —R$^B$—, and —R$^E$ are as defined herein.

In one embodiment, the reaction of step (CAD-1) is performed in an aqueous solvent.

In one embodiment, the reaction of step (CAD-1) comprises reacting a compound of
Formula (E) with a de-esterification agent under conditions suitable to form a compound of Formula (F).

In one embodiment, the reaction of step (CAD-1) comprises reacting a compound of Formula (E) with a de-esterification agent, followed by reaction with an acid (for convenience, referred to herein as a de-esterification acid), under conditions suitable to form a compound of Formula (F).

In one embodiment, the reaction of step (CAD-1) comprises reacting a compound of Formula (E) with a de-esterification agent, followed by acidifying the reaction mixture with an acid (for convenience, referred to herein as a de-esterification acid), under conditions suitable to form a compound of Formula (F).

In one embodiment, the de-esterification agent comprises a base.

In one embodiment, the de-esterification agent comprises an inorganic base.

In one embodiment, the de-esterification agent comprises an alkali metal hydroxide.

In one embodiment, the de-esterification agent comprises sodium hydroxide.

In one embodiment, the de-esterification agent comprises aqueous sodium hydroxide.

In one embodiment, the reaction with a de-esterification agent is performed at a temperature of 30-60° C. In one embodiment, the temperature is 40-50° C.

In one embodiment, the reaction with a de-esterification agent is performed for a period of 10 to 240 minutes. In one embodiment, the period is 20 to 180 minutes. In one embodiment, the period is about 120 minutes.

In one embodiment, the acid (i.e., the de-esterification acid) comprises an inorganic acid.

In one embodiment, the acid (i.e., the de-esterification acid) comprises aqueous acid.

In one embodiment, the acid (i.e., the de-esterification acid) comprises aqueous inorganic acid.

In one embodiment, the acid (i.e., the de-esterification acid) comprises aqueous hydrohalic acid.

In one embodiment, the acid (i.e., the de-esterification acid) comprises aqueous HCl.

In one embodiment, the acid (i.e., the de-esterification acid) comprises 2 M aqueous HCl.

In one embodiment, said acidifying is acidifying to a pH of 1 to 4.

In one embodiment, said acidifying is acidifying to a pH of 1.7 to 2.7.

In one embodiment, said acidifying is acidifying to a pH of about 2.2.

In one embodiment, said reaction with a de-esterification acid and/or said acidifying with a de-esterification acid is performed at a temperature of 30-60° C. In one embodiment, the temperature is 40-50° C.

Alkenyl-Carboxylic Acid Addition (ACAA-1)

In this step, a meta-halo-phenyl-sulfonamide compound (C) is converted to a meta-alkenyl-carboxylic acid-phenyl-sulfonamide compound (F) by reaction with an alkenyl-carboxylic acid (D'), as in, for example:

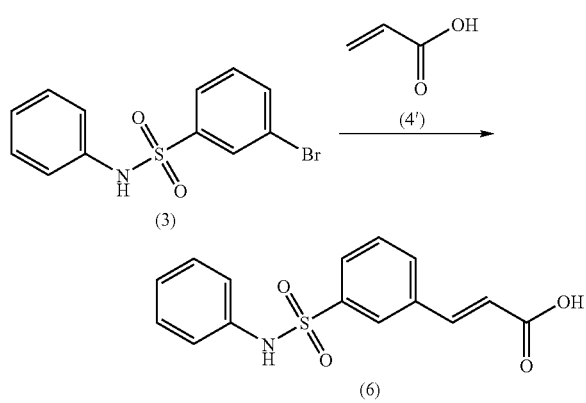

In one embodiment, the step comprises:
(ACAA-1) reacting a compound of Formula (C) with a compound of Formula (D') under conditions suitable to form a compound of Formula (F):

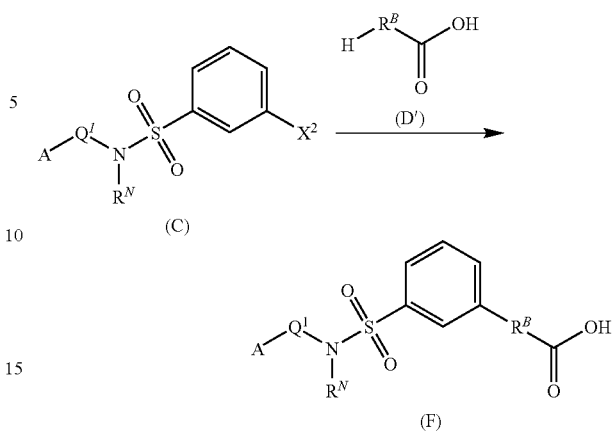

wherein:
-A, -Q¹-, —R$^N$, —X², and —R$^B$— are as defined herein.

In one embodiment, the reaction of step (ACAA-1) is performed in an organic solvent.

In one embodiment, the reaction of step (ACM-1) is performed in an organic solvent comprising N,N-dimethylformamide or N-methylpyrrolidone.

In one embodiment, the reaction of step (ACAA-1) is performed at a temperature of 70-110° C. In one embodiment, the temperature is 80-90° C.

In one embodiment, in the reaction of step (ACAA-1), the compound of Formula (D) is added to the reaction mixture of step (ACAA-1) over a period of 10 to 400 minutes.

In one embodiment, the period is 30 to 300 minutes. In one embodiment, the period is about 165 minutes.

In one embodiment, in the reaction of step (ACAA-1), the molar ratio of the compound Formula (C) to the compound of Formula (D') is 0.5 to 2. In one embodiment, the molar ratio is 0.8 to 1.2.

Catalyst:

In one embodiment, the reaction of step (ACM-1) is performed in the presence of a catalyst.

In one embodiment, the catalyst is a palladium catalyst.

In one embodiment, the catalyst is a palladium (0) catalyst.

In one embodiment, the palladium (0) catalyst is added to the reaction mixture of step (ACAA-1), prior to the addition of the compound of Formula (D').

In one embodiment, the palladium (0) catalyst is prepared in situ, in the reaction mixture of step (ACAA-1), prior to the addition of the compound of Formula (D').

In one embodiment, the palladium (0) catalyst is prepared by reaction of a palladium (II) compound, e.g., under conditions suitable to form said palladium (0) catalyst.

For example, the palladium (0) catalyst may be "ligand free" or "homeopathic ligand-free" palladium (0), as is well known in the art. Alternatively, the palladium (0) catalyst may be stabilized using one or more ligands, for example, phosphines or phosphites, as is also well known in the art.

In one embodiment, the palladium (0) catalyst is prepared by reaction of a palladium (II) compound and a phosphine or a phosphite, e.g., under conditions suitable to form said palladium (0) catalyst.

In one embodiment, the palladium (0) catalyst is prepared by reaction of a palladium (II) compound and a phosphine, e.g., under conditions suitable to form said palladium (0) catalyst.

In one embodiment, the palladium (0) catalyst is prepared by reaction of a palladium (II) compound, a phosphine or a phosphite, and a base (for convenience, referred to as an "assisting base"), e.g., under conditions suitable to form said palladium (0) catalyst.

In one embodiment, the palladium (0) catalyst is prepared by reaction of a palladium (II) compound, a phosphine, and a base (for convenience, referred to as an "assisting base"), e.g., under conditions suitable to form said palladium (0) catalyst.

In one embodiment, the palladium (0) catalyst is prepared in situ, in the reaction mixture of step (ACAA-1), by reaction of a palladium (II) compound and a phosphine or a phosphite, e.g., under conditions suitable to form said palladium (0) catalyst.

In one embodiment, the palladium (0) catalyst is prepared in situ, in the reaction mixture of step (ACAA-1), by reaction of a palladium (II) compound and a phosphine, e.g., under conditions suitable to form said palladium (0) catalyst.

In one embodiment, the palladium (0) catalyst is prepared in situ, in the reaction mixture of step (ACAA-1), by reaction of a palladium (II) compound, a phosphine or a phosphite, and a base (again, for convenience, referred to as an "assisting base"), e.g., under conditions suitable to form said palladium (0) catalyst.

In one embodiment, the palladium (0) catalyst is prepared in situ, in the reaction mixture of step (ACAA-1), by reaction of a palladium (II) compound, a phosphine, and a base (again, for convenience, referred to as an "assisting base"), e.g., under conditions suitable to form said palladium (0) catalyst.

In one embodiment, the step (ACAA-1) comprises:
(ACAA-1a) adding a palladium (II) compound and a phosphine to a reaction mixture comprising the compound of Formula (C) under conditions suitable to form a palladium (0) catalyst; and subsequently
(ACAA-1b) adding the compound of Formula (D') under conditions suitable to form a compound of Formula (F).

In one embodiment, the step (ACAA-1) comprises:
(ACAA-1aa) adding a palladium (II) compound, a phosphine, and a base (again, for convenience, referred to as an "assisting base") to a reaction mixture comprising the compound of Formula (C) under conditions suitable to form a palladium (0) catalyst; and subsequently
(ACAA-1b) adding to the reaction mixture produced in step (ACAA-1aa) the compound of Formula (D') under conditions suitable to form a compound of Formula (F).

In one embodiment, the palladium (II) compound is palladium (II) acetate.

Examples of suitable phosphines include the following:

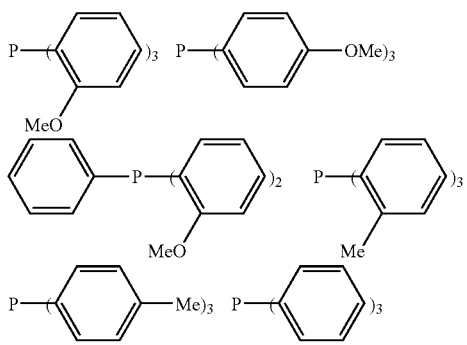

In one embodiment, the phosphine is a triarylphosphine.
In one embodiment, the phosphine is triphenylphosphine or tri(tolyl)phosphine.
In one embodiment, the phosphine is tri(o-tolyl)phosphine.

Examples of suitable phosphites include the following:

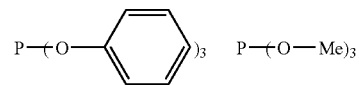

In one embodiment, the base (i.e., the assisting base) is an organic base.

In one embodiment, the base (i.e., the assisting base) is tri($C_{1-4}$alkyl)amine.

In one embodiment, the base (i.e., the assisting base) is triethylamine or tributylamine.

In one embodiment, the base (i.e., the assisting base) is triethylamine.

In one embodiment, the base (i.e., the assisting base) is tributylamine.

In one embodiment, the reaction to form said palladium (0) catalyst (e.g., the reaction of step (ACAA-1a) or (ACAA-1aa)) is performed at a temperature of 35-65° C. In one embodiment, the temperature is 45-55° C.

In one embodiment, the reaction to form said palladium (0) catalyst (e.g., the reaction of step (ACAA-1a) or (ACAA-1aa)) further comprises degassing the reaction mixture after formation of the palladium (0) catalyst.

Optional Purification ($PUR^F$)

In this optional step, a meta-alkenyl-carboxylic acid-phenyl-sulfonamide compound (F) is purified.

In one embodiment, the step comprises:
($PUR^F$) optionally purifying a compound of Formula (F), as defined herein.

In one embodiment, this optional step is included (i.e., is performed; is not optional).

In one embodiment, this optional step is omitted.

In one embodiment, the step ($PUR^F$) comprises one or more steps selected from:
a step of purifying a compound of Formula (F) by filtration;
a step of purifying a compound of Formula (F) by precipitation; and
a step of purifying a compound of Formula (F) by recrystallisation.

In one embodiment, the step ($PUR^F$) comprises (or further comprises) a step of purifying a compound of Formula (F) by filtration.

In one embodiment, the step ($PUR^F$) comprises (or further comprises) a step of purifying a compound of Formula (F) by precipitation.

In one embodiment, the step ($PUR^F$) comprises (or further comprises) a step of purifying a compound of Formula (F) by recrystallisation.

For example, in one embodiment, the step ($PUR^F$) comprises the following steps, in order:
a step of purifying a compound of Formula (F) by precipitation; and
a step of purifying a compound of Formula (F) by recrystallisation.

Purification by Filtration:

In one embodiment, the purification by filtration is filtering a mixture of the compound of Formula (F) and a filtration solvent, and collecting the filtrate.

In one embodiment, the purification by filtration is by forming a mixture of the compound of Formula (F) with a filtration solvent, filtering the mixture, and collecting the filtrate.

In one embodiment, the filtration solvent comprises an organic solvent.

In one embodiment, the filtration solvent comprises tetrahydrofuran.

In one embodiment, the filtration is performed at a temperature of 35-65° C.

In one embodiment, the filtration is performed at a temperature of 45-55° C.

Purification by Precipitation:

In one embodiment, the purification by precipitation is by cooling a liquid mixture comprising dissolved compound of Formula (F) to form a precipitate comprising the compound of Formula (F), and collecting the precipitate (e.g., by filtration).

In one embodiment, the purification by precipitation is by cooling a liquid mixture comprising dissolved compound of Formula (F) to form a precipitate comprising the compound of Formula (F), collecting the precipitate (e.g., by filtration), and washing the collected precipitate (e.g., with water).

In one embodiment, the purification by precipitation is by cooling a liquid mixture comprising dissolved compound of Formula (F) to form a precipitate comprising the compound of Formula (F), collecting the precipitate (e.g., by filtration), and drying the collected precipitate (e.g., in an oven).

In one embodiment, the purification by precipitation is by cooling a liquid mixture comprising dissolved compound of Formula (F) to form a precipitate comprising the compound of Formula (F), collecting the precipitate (e.g., by filtration), washing the collected precipitate (e.g., with water), and drying the washed precipitate (e.g., in an oven).

In one embodiment, the cooling is to a temperature of 10-40° C.

In one embodiment, the cooling is to a temperature of 10-30° C.

In one embodiment, the cooling is to a temperature of 20-30° C.

In one embodiment, the cooling is for a time of 10 minutes to 6 hours.

In one embodiment, the cooling is for a time of about 2 hours.

In one embodiment, the drying is at a temperature of 35-65° C.

In one embodiment, the drying is at a temperature of 45-55° C.

In one embodiment, the drying is for a time of 1 hour to 7 days.

In one embodiment, the drying is for a time of about 1 day.

In one embodiment, the drying is under vacuum.

Purification by Recrystallisation:

In one embodiment, the recrystallisation is by dissolving the compound of Formula (F) in a recrystallisation solvent, cooling the resulting solution to form a precipitate comprising the compound of Formula (F), and collecting the precipitate (e.g., by filtration).

In one embodiment, the recrystallisation is by dissolving the compound of Formula (F) in a recrystallisation solvent, cooling the resulting solution to form a precipitate comprising the compound of Formula (F), collecting the precipitate (e.g., by filtration), and washing the collected precipitate (e.g., with recrystallisation solvent).

In one embodiment, the recrystallisation is by dissolving the compound of Formula (F) in a recrystallisation solvent, cooling the resulting solution to form a precipitate comprising the compound of Formula (F), collecting the precipitate (e.g., by filtration), washing the collected precipitate (e.g., with recrystallisation solvent), and drying the washed precipitate (e.g., in an oven).

In one embodiment, the recrystallisation is by dissolving the compound of Formula (F) in a recrystallisation solvent, cooling the resulting solution to form a precipitate comprising the compound of Formula (F), collecting the precipitate (e.g., by filtration), and drying the collected precipitate (e.g., in an oven).

In one embodiment, the step of dissolving the compound of Formula (F) in a recrystallisation solvent includes the step of heating a mixture of the compound of Formula (F) and the recrystallisation solvent, before the step of cooling the resulting solution to form a precipitate comprising the compound of Formula (F).

In one embodiment, the recrystallisation solvent is an organic solvent.

In one embodiment, the recrystallisation solvent is acetonitrile.

In one embodiment, the heating is heating to reflux.

In one embodiment, the heating is heating to about 80° C.

In one embodiment, the heating is for a time of 10 minutes to 6 hours.

In one embodiment, the heating is for a time of about 2 hours.

In one embodiment, the cooling is to a temperature of 0-20° C.

In one embodiment, the cooling is to a temperature of 0-10° C.

In one embodiment, the cooling is for a time of 10 minutes to 12 hours.

In one embodiment, the cooling is for a time of about 6 hours.

In one embodiment, the drying is at a temperature of 35-65° C.

In one embodiment, the drying is at a temperature of 45-55° C.

In one embodiment, the drying is for a time of 1 hour to 7 days.

In one embodiment, the drying is for a time of about 1 day.

Hydroxamic Acid Formation (HAF)

In this step, a meta-alkenyl-carboxylic acid-phenyl-sulfonamide compound (F) is converted to a meta-alkenyl-hydroxamic acid-phenyl-sulfonamide compound (G), as in, for example:

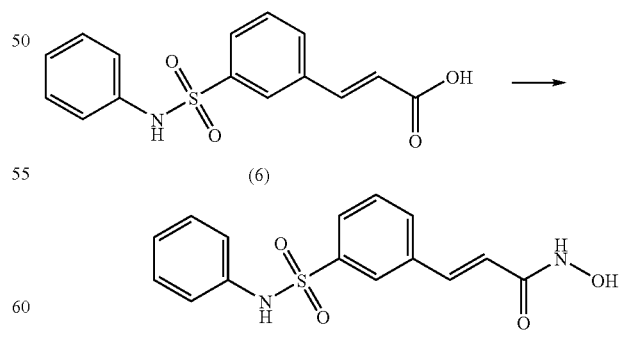

In one embodiment, the step comprises:

(HAF-1) reacting a compound of Formula (F) under conditions suitable to form a compound of Formula (G):

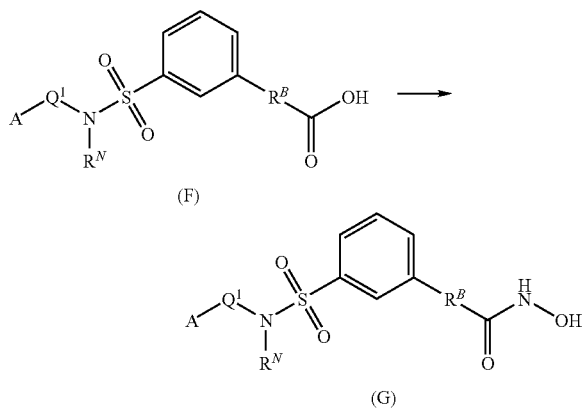

wherein:
-A, -Q¹-, —$R^N$, —$R^B$—, and —$R^E$ are as defined herein.

In one embodiment, the step (HAF-1) comprises the following steps, in order:
(HAF-1a) reacting a compound of Formula (F) with thionyl chloride ($SOCl_2$) or oxalyl chloride ($C_2O_2Cl_2$);
(HAF-1b) reacting the product of step (HAF-1a) with hydroxylamine ($NH_2OH$);
under conditions suitable to form a compound of Formula (G).

In one embodiment, the step (HAF-1) comprises the following steps, in order:
(HAF-1a) reacting a compound of Formula (F) with thionyl chloride ($SOCl_2$);
(HAF-1b) reacting the product of step (HAF-1a) with hydroxylamine ($NH_2OH$);
under conditions suitable to form a compound of Formula (G).

In one embodiment, the step (HAF-1) comprises the following steps, in order:
(HAF-1a) reacting a compound of Formula (F) with oxalyl chloride ($C_2O_2Cl_2$);
(HAF-1b) reacting the product of step (HAF-1a) with hydroxylamine ($NH_2OH$);
under conditions suitable to form a compound of Formula (G).

In one embodiment, the reaction of step (HAF-1a) is performed in an organic solvent.

In one embodiment, the reaction of step (HAF-1a) is performed in an organic solvent comprising isopropyl acetate.

In one embodiment, the reaction of step (HAF-1a) is performed in an organic solvent that is isopropyl acetate.

In one embodiment, the reaction of step (HAF-1a) is performed in the presence of a base.

In one embodiment, the reaction of step (HAF-1a) is performed in the presence of an organic base.

In one embodiment, the reaction of step (HAF-1a) is performed in the presence of DBU.

In one embodiment, the reaction of step (HAF-1a) is performed at a temperature of 10-40° C. In one embodiment, the temperature is 20-30° C.

In one embodiment, the reaction of step (HAF-1a) is performed for a period of 1 to 30 hours. In one embodiment, the period is 10 to 25 hours. In one embodiment, the period is about 18.5 hours.

In one embodiment, the hydroxylamine ($NH_2OH$) is provided as hydroxylamine hydrochloride ($NH_2OH.HCl$).

In one embodiment, the hydroxylamine (or hydroxylamine hydrochloride) used in step (HAF-1b) is provided as aqueous hydroxylamine (or aqueous hydroxylamine hydrochloride).

In one embodiment, the hydroxylamine (or hydroxylamine hydrochloride) used in step (HAF-1b) is provided as a mixture of aqueous hydroxylamine (or aqueous hydroxylamine hydrochloride) and an organic solvent.

In one embodiment, the hydroxylamine (or hydroxylamine hydrochloride) used in step (HAF-1b) is provided as a mixture of aqueous hydroxylamine (or aqueous hydroxylamine hydrochloride) and THF.

In one embodiment, the aqueous hydroxylamine used in step (HAF-1b) is provided at a concentration of 5-50% (w/w). In one embodiment, the concentration is 5-20% (w/w). In one embodiment, the concentration is 10% (w/w).

In one embodiment, the hydroxylamine used in step (HAF-1b) is provided at a temperature of 0-30° C. In one embodiment, the temperature is 0-20° C. In one embodiment, the temperature is 0-10° C.

In one embodiment, the reaction of step (HAF-1b) is performed at a temperature of 0-20° C. In one embodiment, the temperature is 0-10° C.

In one embodiment, the reaction of step (HAF-1b) is performed for a period of 5 to 240 minutes. In one embodiment, the period is 10 to 120 hours. In one embodiment, the period is about 60 minutes.

Optional Purification ($PUR^G$)

In this optional step, a meta-alkenyl-hydroxamic acid-phenyl-sulfonamide compound (G) is purified.

In one embodiment, the step comprises:
($PUR^G$) optionally purifying a compound of Formula (G), as defined herein.

In one embodiment, this optional step is included (i.e., is performed; is not optional).

In one embodiment, this optional step is omitted.

In one embodiment, the step ($PUR^G$) comprises one or more steps selected from:
a step of purifying a compound of Formula (G) by filtration;
a step of purifying a compound of Formula (G) by precipitation; and
a step of purifying a compound of Formula (G) by recrystallisation.

In one embodiment, the step ($PUR^G$) comprises (or further comprises) a step of purifying a compound of Formula (G) by filtration.

In one embodiment, the step ($PUR^G$) comprises (or further comprises) a step of purifying a compound of Formula (G) by precipitation.

In one embodiment, the step ($PUR^G$) comprises (or further comprises) a step of purifying a compound of Formula (G) by recrystallisation.

Purification by Filtration:

In one embodiment, the purification by filtration is filtering a mixture of the compound of Formula (G) and a filtration solvent, and collecting the filtrate.

In one embodiment, the purification by filtration is by forming a mixture of the compound of Formula (G) with a filtration solvent, filtering the mixture, and collecting the filtrate.

In one embodiment, the filtration solvent comprises an organic solvent.

In one embodiment, the filtration solvent comprises isopropyl acetate.

In one embodiment, the filtration is performed at a temperature of 35-65° C.

In one embodiment, the filtration is performed at a temperature of 45-55° C.

Purification by Precipitation:

In one embodiment, the purification by precipitation is by concentrating a solution comprising dissolved compound of Formula (G) to form a precipitate comprising the compound of Formula (G), and collecting the precipitate (e.g., by filtration).

In one embodiment, the purification by precipitation is by concentrating a solution comprising dissolved compound of Formula (G) to form a precipitate comprising the compound of Formula (G), collecting the precipitate (e.g., by filtration), and washing the collected precipitate (e.g., with heptanes).

In one embodiment, the purification by precipitation is by concentrating a solution comprising dissolved compound of Formula (G) to form a precipitate comprising the compound of Formula (G), collecting the precipitate (e.g., by filtration), and drying the collected precipitate (e.g., in an oven).

In one embodiment, the purification by precipitation is by concentrating a solution comprising dissolved compound of Formula (G) to form a precipitate comprising the compound of Formula (G), collecting the precipitate (e.g., by filtration), washing the collected precipitate (e.g., with heptanes), and drying the washed precipitate (e.g., in an oven).

In one embodiment, the solution comprising dissolved compound of Formula (G) is a solution of the compound of Formula (G) in an organic solvent.

In one embodiment, the solution comprising dissolved compound of Formula (G) is the organic fraction of the reaction mixture produced in step (HAF-1b).

In one embodiment, the concentrating is by removing solvent from the solution comprising dissolved compound of Formula (G). In one embodiment, the removing is performed at a temperature of less than about 30° C.

In one embodiment, the concentrating is by distilling solvent from the solution comprising dissolved compound of Formula (G). In one embodiment, the distilling is performed at a temperature of less than about 30° C.

In one embodiment, the drying is at a temperature of 35-65° C.

In one embodiment, the drying is at a temperature of 45-55° C.

In one embodiment, the drying is for a time of 1 hour to 7 days.

In one embodiment, the drying is performed under vacuum with a slight nitrogen bleed.

Purification by Recrystallisation:

In one embodiment, the recrystallisation is by dissolving the compound of Formula (G) in a recrystallisation solvent, cooling the resulting solution to form a precipitate comprising the compound of Formula (G), and collecting the precipitate (e.g., by filtration).

In one embodiment, the recrystallisation is by dissolving the compound of Formula (G) in a recrystallisation solvent, cooling the resulting solution to form a precipitate comprising the compound of Formula (G), collecting the precipitate (e.g., by filtration), and washing the collected precipitate (e.g., with recrystallisation solvent).

In one embodiment, the recrystallisation is by dissolving the compound of Formula (G) in a recrystallisation solvent, cooling the resulting solution to form a precipitate comprising the compound of Formula (G), collecting the precipitate (e.g., by filtration), washing the collected precipitate (e.g., with recrystallisation solvent), and drying the washed precipitate (e.g., in an oven).

In one embodiment, the recrystallisation is by dissolving the compound of Formula (G) in a recrystallisation solvent, cooling the resulting solution to form a precipitate comprising the compound of Formula (G), collecting the precipitate (e.g., by filtration), and drying the collected precipitate (e.g., in an oven).

In one embodiment, the step of dissolving the compound of Formula (G) in a recrystallisation solvent includes the step of heating a mixture of the compound of Formula (G) and the recrystallisation solvent, before the step of cooling the resulting solution to form a precipitate comprising the compound of Formula (G).

In one embodiment, the recrystallisation is by dissolving the compound of Formula (G) in a recrystallisation solvent in the presence of a base, cooling the resulting solution to form a precipitate comprising the compound of Formula (G), and collecting the precipitate (e.g., by filtration).

In one embodiment, the recrystallisation is by dissolving the compound of Formula (G) in a recrystallisation solvent in the presence of a base, cooling the resulting solution to form a precipitate comprising the compound of Formula (G), collecting the precipitate (e.g., by filtration), and washing the collected precipitate (e.g., with recrystallisation solvent).

In one embodiment, the recrystallisation is by dissolving the compound of Formula (G) in a recrystallisation solvent in the presence of a base, cooling the resulting solution to form a precipitate comprising the compound of Formula (G), collecting the precipitate (e.g., by filtration), washing the collected precipitate (e.g., with recrystallisation solvent), and drying the washed precipitate (e.g., in an oven).

In one embodiment, the recrystallisation is by dissolving the compound of Formula (G) in a recrystallisation solvent in the presence of a base, cooling the resulting solution to form a precipitate comprising the compound of Formula (G), collecting the precipitate (e.g., by filtration), and drying the collected precipitate (e.g., in an oven).

In one embodiment, the step of dissolving the compound of Formula (G) in a recrystallisation solvent includes the step of heating a mixture of the compound of Formula (G) and the recrystallisation solvent in the presence of a base, before the step of cooling the resulting solution to form a precipitate comprising the compound of Formula (G).

In one embodiment, the recrystallisation solvent is an organic solvent.

In one embodiment, the recrystallisation solvent is ethanol/water (e.g., 1:1).

In one embodiment, the base (e.g., the recrystallisation base) is an inorganic base.

In one embodiment, the base (e.g., the recrystallisation base) is an organic base.

In one embodiment, the base (e.g., the recrystallisation base) is sodium bicarbonate.

In one embodiment, the base (e.g., the recrystallisation base) is 5-10 mol % sodium bicarbonate (with respect to the compound of Formula (G)).

In one embodiment, the heating is heating to reflux.

In one embodiment, the heating is heating to about 70° C.

In one embodiment, the heating is for a time of 10 minutes to 6 hours.

In one embodiment, the heating is for a time of about 2 hours.

In one embodiment, the cooling is to a temperature of 0-20° C.

In one embodiment, the cooling is to a temperature of 0-10° C.

In one embodiment, the cooling is for a time of 10 minutes to 12 hours.

In one embodiment, the cooling is for a time of about 6 hours.

In one embodiment, the drying is at a temperature of 35-65° C.

In one embodiment, the drying is at a temperature of 45-55° C.

In one embodiment, the drying is for a time of 1 hour to 7 days.

In one embodiment, the drying is for a time of about 1 day.

Compounds

Another aspect of the present invention pertains to a compound of Formula (G), or a salt, hydrate, or solvate thereof, obtained by a method of synthesis, as described herein.

Another aspect of the present invention pertains to a compound of Formula (F), or a salt, hydrate, or solvate thereof, obtained by a method of synthesis, as described herein.

Another aspect of the present invention pertains to a compound of Formula (E), or a salt, hydrate, or solvate thereof, obtained by a method of synthesis, as described herein.

Another aspect of the present invention pertains to a compound of Formula (C), or a salt, hydrate, or solvate thereof, obtained by a method of synthesis, as described herein.

Compounds of Formula (F), (E), and (C), and salts, hydrates, and solvates thereof, are useful, for example, as chemical intermediates, for example, in the synthesis of compounds of Formula (G), and salts, hydrates, and solvates thereof.

Medical Use

Another aspect of the present invention pertains to a compound of Formula (G) obtained by a method of synthesis, as described herein, for use in a method of treatment of the human or animal body.

Another aspect of the present invention pertains to a compound of Formula (G) obtained by a method of synthesis, as described herein, for use in a method of treatment of a disease or disorder.

Another aspect of the present invention pertains to use of a compound of Formula (G) obtained by a method of synthesis, as described herein, in the manufacture of a medicament for the treatment of a disease or disorder.

Another aspect of the present invention pertains to a method of treatment of a disease or disorder in a patient, comprising administering to said patient a therapeutically-effective amount of a compound of Formula (G) obtained by a method of synthesis, as described herein.

In one embodiment, the disease or disorder is a disease or disorder which is mediated by HDAC.

In one embodiment, the disease or disorder is a disease or disorder which is treatable or known to be treatable with an HDAC inhibitor.

In one embodiment, the disease or disorder is a proliferative condition.

In one embodiment, the disease or disorder is cancer.

In one embodiment, the disease or disorder is psoriasis.

In one embodiment, the disease or disorder is malaria.

EXAMPLES

The following examples are provided solely to illustrate the present invention and are not intended to limit the scope of the invention, as described herein.

The methods of synthesis of the present invention are exemplified below for a representative compound, PXD101. The method is illustrated in the following scheme.

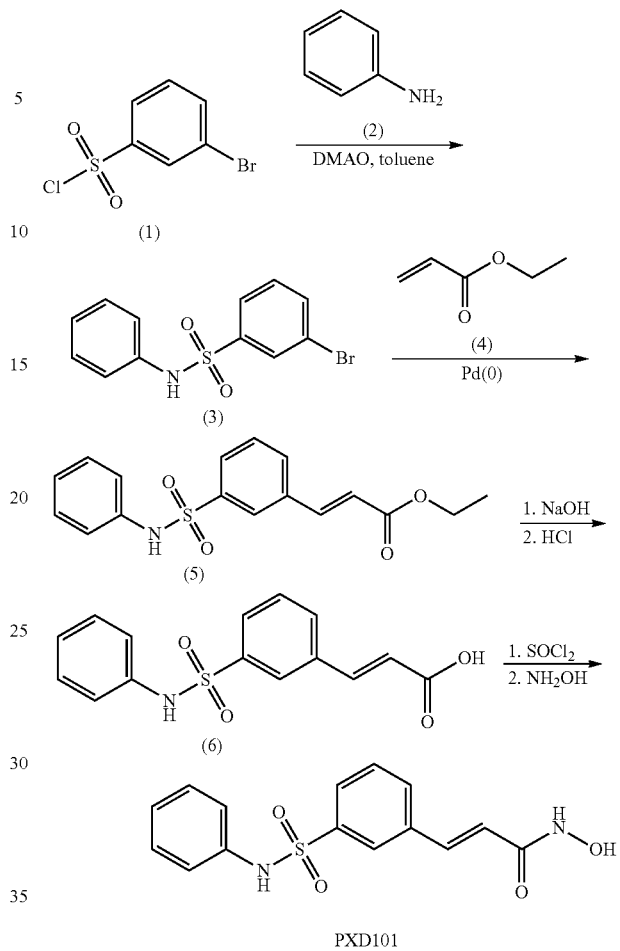

Synthesis 1

3-Bromo-N-phenyl-benzenesulfonamide (3)

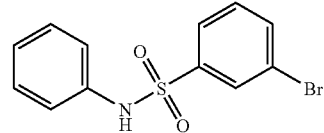 [SMILES: O=S(=O)(Nc1ccccc1)c1cccc(Br)c1]

To a 30 gallon (~136 L) reactor was charged aniline (2) (4.01 kg; 93.13 g/mol; 43 mol), toluene (25 L), and 4-(dimethylamino)pyridine (DMAP) (12 g), and the mixture was heated to 50-60° C. 3-Bromobenzenesulfonyl chloride (1) (5 kg; 255.52 g/mol; 19.6 mol) was charged into the reactor over 30 minutes at 50-60° C. and progress of the reaction was monitored by HPLC. After 19 hours, toluene (5 L) was added due to losses overnight through the vent line and the reaction was deemed to be complete with no compound (1) being detected by HPLC. The reaction mixture was diluted with toluene (10 L) and then quenched with 2 M aqueous hydrochloric acid (20 L). The organic and aqueous layers were separated, the aqueous layer was discarded, and the organic layer was washed with water (20 L), and then 5% (w/w) sodium bicarbonate solution (20 L), while maintaining the batch temperature at 45-55° C. The batch was then used in the next synthesis.

Synthesis 2

(E)-3-(3-Phenylsulfamoyl-phenyl)-acrylic acid ethyl ester (5)

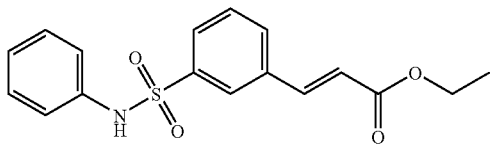 [SMILES: CCOC(=O)/C=C/c1cccc(S(=O)(=O)Nc2ccccc2)c1]

To the batch containing 3-bromo-N-phenyl-benzenesulfonamide (3) (the treated organic layer obtained in the previous synthesis) was added triethylamine (2.97 kg; 101.19 g/mol; 29.4 mol), tri(o-tolyl)phosphine (119 g; 304.37 g/mol; 0.4 mol), and palladium (II) acetate (44 g; 224.51 g/mol; 0.2 mol), and the resulting mixture was degassed four times with a vacuum/nitrogen purge at 45-55° C. Catalytic palladium (0) was formed in situ. The batch was then heated to 80-90° C. and ethyl acrylate (4) (2.16 kg; 100.12 g/mol; 21.6 mol) was slowly added over 2.75 hours. The batch was sampled after a further 2 hours and was deemed to be complete with no compound (3) being detected by HPLC. The batch was cooled to 45-55° C. and for convenience was left at this temperature overnight.

The batch was then reduced in volume under vacuum to 20-25 L, at a batch temperature of 45-55° C., and ethyl acetate (20 L) was added. The batch was filtered and the residue washed with ethyl acetate (3.5 L). The residue was discarded and the filtrates were sent to a 100 gallon (~454 L) reactor, which had been pre-heated to 60° C. The 30 gallon (~136 L) reactor was then cleaned to remove any residual Pd, while the batch in the 100 gallon (~454 L) reactor was washed with 2 M aqueous hydrochloric acid and water at 45-55° C. Once the washes were complete and the 30 gallon (~136 L) reactor was clean, the batch was transferred from the 100 gallon (~454 L) reactor back to the 30 gallon (~136 L) reactor and the solvent was swapped under vacuum from ethyl acetate/toluene to toluene while maintaining a batch temperature of 45-55° C. (the volume was reduced to 20-25 L). At this point, the batch had precipitated and heptanes (10 L) were added to re-dissolve it. The batch was then cooled to 0-10° C. and held at this temperature over the weekend in order to precipitate the product. The batch was filtered and the residue was washed with heptanes (5 L). A sample of the wet-cake was taken for Pd analysis. The Pd content of the crude product (5) was determined to be 12.9 ppm.

The wet-cake was then charged back into the 30 gallon (~136 L) reactor along with ethyl acetate (50 L) and heated to 40-50° C. in order to obtain a solution. A sparkler filter loaded with 12 impregnated Darco G60® carbon pads was then connected to the reactor and the solution was pumped around in a loop through the sparkler filter. After 1 hour, a sample was taken and evaporated to dryness and analysed for Pd content. The amount of Pd was found to be 1.4 ppm. A second sample was taken after 2 hours and evaporated to dryness and analysed for Pd content. The amount of Pd had been reduced to 0.6 ppm. The batch was blown back into the reactor and held at 40-50° C. overnight before the solvent was swapped under vacuum from ethyl acetate to toluene while maintaining a batch temperature of 45-55° C. (the volume was reduced to 20-25 L). At this point, the batch had precipitated and heptanes (10 L) were added to re-dissolve it and the batch was cooled to 0-10° C. and held at this temperature overnight in order to precipitate the product. The batch was filtered and the residue was washed with heptanes (5 L). The filtrate was discarded and the residue was dried at 45-55° C. under vacuum for 25 hours. A first lot of the title compound (5) was obtained as an off-white solid (4.48 kg, 69% overall yield from 3-bromobenzenesulfonyl chloride (1)) with a Pd content of 0.4 ppm and a purity of 99.22% (AUC) by HPLC.

Synthesis 3

(E)-3-(3-Phenylsulfamoyl-phenyl)-acrylic acid (6)

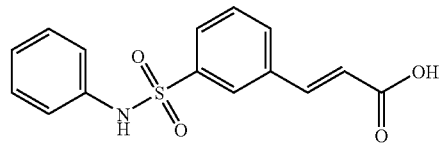 [SMILES: O=C(O)/C=C/c1cccc(S(=O)(=O)Nc2ccccc2)c1]

To the 30 gallon (~136 L) reactor was charged the (E)-3-(3-phenylsulfamoyl-phenyl)-acrylic acid ethyl ester (5) (4.48 kg; 331.39 g/mol; 13.5 mol) along with 2 M aqueous sodium hydroxide (17.76 L; ~35 mol). The mixture was heated to 40-50° C. and held at this temperature for 2 hours before sampling, at which point the reaction was deemed to be complete with no compound (5) being detected by HPLC. The batch was adjusted to pH 2.2 using 1 M aqueous hydrochloric acid while maintaining the batch temperature between 40-50° C. The product had precipitated and the batch was cooled to 20-30° C. and held at this temperature for 1 hour before filtering and washing the cake with water (8.9 L). The filtrate was discarded. The batch was allowed to condition on the filter overnight before being charged back into the reactor and slurried in water (44.4 L) at 40-50° C. for 2 hours. The batch was cooled to 15-20° C., held for 1 hour, and then filtered and the residue washed with water (8.9 L). The filtrate was discarded. The crude title compound (6) was transferred to an oven for drying at 45-55° C. under vacuum with a slight nitrogen bleed for 5 days (this was done for convenience) to give a white solid (3.93 kg, 97% yield). The moisture content of the crude material was measured using Karl Fischer (KF) titration and found to be <0.1% (w/w). To the 30 gallon (~136 L) reactor was charged the crude compound (6) along with acetonitrile (47.2 L). The batch was heated to reflux (about 80° C.) and held at reflux for 2 hours before cooling to 0-10° C. and holding at this temperature overnight in order to precipitate the product. The batch was filtered and the residue was washed with cold acetonitrile (7.9 L). The filtrate was discarded and the residue was dried under vacuum at 45-55° C. for 21.5 hours. The title compound (6) was obtained as a fluffy white solid (3.37 kg, 84% yield with respect to compound (5)) with a purity of 99.89% (AUC) by HPLC.

Synthesis 4

(E)-N-Hydroxy-3-(3-phenylsulfamoyl-phenyl)-acrylamide (PXD101)

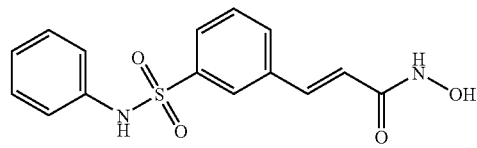 [SMILES: O=C(/C=C/c1cccc(S(=O)(=O)Nc2ccccc2)c1)NO]

To the 30 gallon (~136 L) reactor was charged (E)-3-(3-phenylsulfamoyl-phenyl)-acrylic acid (6) (3.37 kg; 303.34 g/mol; 11.1 mol) and a pre-mixed solution of 1,8-diazabicyclo[5.4.0]undec-7-ene (DBU) in isopropyl acetate (IPAc) (27 g in 30 L; 152.24 g/mol; 0.18 mol). The slurry was stirred and thionyl chloride (SOCl$_2$) (960 mL; density ~1.631 g/mL; 118.97 g/mol; ~13 mol) was added to the reaction mixture and the batch was stirred at 20-30° C. overnight. After 18.5 hours, the batch was sampled and deemed to be complete with no compound (6) being detected by HPLC. The resulting solution was transferred to a 100 L Schott reactor for temporary storage while the 30 gallon (~136 L) reactor was rinsed with isopropyl acetate (IPAc) and water. Deionized water (28.9 L) was then added to the 30 gallon (~136 L) reactor followed by 50% (w/w) hydroxylamine (6.57 L; ~1.078 g/mL; 33.03 g/mol; ~214 mol) and another charge of deionized water (1.66 L) to rinse the lines free of hydroxylamine to make a 10% (w/w) hydroxylamine solution. Tetrahydrofuran (THF) (6.64 L) was then charged to the 30 gallon (~136 L) reactor and the mixture was stirred and cooled to 0-10° C. The acid chloride solution (from the 100 L Schott reactor) was then slowly charged into the hydroxylamine solution over 1 hour maintaining a batch temperature of 0-10° C. during the addition. The batch was then allowed to warm to 20-30° C. The aqueous layer was separated and discarded. The organic layer was then reduced in volume under vacuum while maintaining a batch temperature of less than 30° C. The intention was to distill out 10-13 L of solvent, but this level was overshot. A larger volume of isopropyl acetate (IPAc) (16.6 L) was added and about 6 L of solvent was distilled out. The batch had precipitated and heptanes (24.9 L) were added and the batch was held at 20-30° C. overnight. The batch was filtered and the residue was washed with heptanes (6.64 L). The filtrate was discarded and the residue was dried at 45-55° C. under vacuum with a slight nitrogen bleed over the weekend. The title compound (PXD101) was obtained as a light orange solid (3.11 kg, 89% yield with respect to compound (6)) with a purity of 99.25% (AUC) by HPLC.

The title compound (PXD101) (1.2 kg, 3.77 mol) was dissolved in 8 volumes of 1:1 (EtOH/water) at 60° C. Sodium bicarbonate (15.8 g, 5 mol %) was added to the solution. Water (HPLC grade) was then added at a rate of 65 mL/min while keeping the internal temperature >57° C. After water (6.6 L) had been added, crystals started to form and the water addition was stopped. The reaction mixture was then cooled at a rate of 10° C./90 min to a temperature of 0-10° C. and then stirred at ambient temperature overnight. The crystals were then filtered and collected. The filter cake was washed by slurrying in water (2×1.2 L) and then dried in an oven at 45° C. for 60 hours with a slight nitrogen bleed. 1.048 kg (87% recovery) of a light orange solid was recovered. Microscopy and XRPD data showed a conglomerate of irregularly shaped birefringant crystalline particles. The compound was found to contain 0.02% water.

As discussed above:

the yield of compound (5) with respect to compound (1) was 69%.

the yield of compound (6) with respect to compound (5) was 84%.

the yield of PXD101 with respect to compound (6) was 89%.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

The invention claimed is:

1. A method for the synthesis of a compound of the following formula or a pharmaceutically acceptable salt thereof:

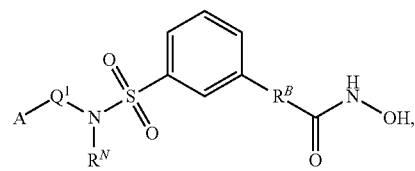

wherein:

-A is independently -A$^1$, -A$^2$, -A$^3$, or -A$^4$;

-A$^1$ is independently C$_{6-10}$carboaryl, and is optionally substituted;

-A$^2$ is independently C$_{5-10}$heteroaryl, and is optionally substituted;

-A$^3$ is independently C$_{5-7}$cycloalkyl, and is optionally substituted;

-A$^4$ is independently C$_{5-7}$heterocyclic, and is optionally substituted;

-Q$^1$- is independently a covalent bond or —R$^A$—;

—R$^A$- is independently —R$^{A1}$— or —R$^{A2}$—;

—R$^{A1}$— is independently aliphatic C$_{2-6}$alkylene, and is optionally substituted;

—R$^{A2}$— is independently aliphatic C$_{2-6}$alkenylene, and is optionally substituted;

—R$^N$ is independently —H, saturated aliphatic C$_{1-4}$-alkyl, phenyl, or benzyl; and —R$^B$— is independently —R$^{B1}$— or —R$^{B2}$—;

—R$^{B1}$— is independently aliphatic C$_{2-6}$alkenylene, and is optionally substituted;

—R$^{B2}$— is independently aliphatic C$_{2-6}$alkynyl-alkenylene, and is optionally substituted;

said method comprising, in order:

(a) an alkenyl-acid addition (AAA) step comprising either (i): in order:

reacting a compound of Formula (C):

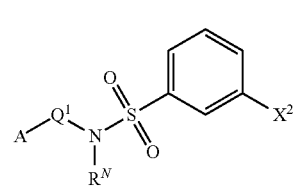

with a compound of Formula (D):

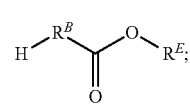

to form a compound of Formula (E):

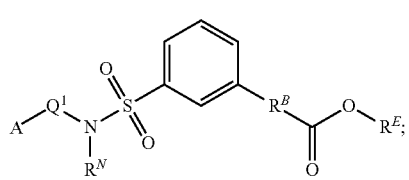
(E)

an optional purification (PUR$^E$) step comprising optionally purifying said compound of formula (E); and
forming a compound of formula (F):

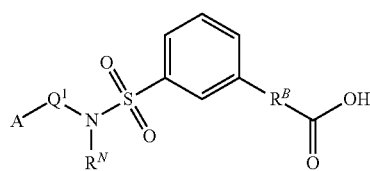
(F)

either:
(i) by a carboxylic acid deprotection (CAD-1) step comprising reacting said compound of Formula (E):

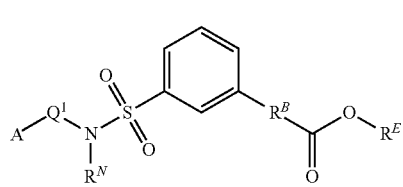
(E)

with a de-esterification agent, wherein the de-esterification agent is an acid, or an inorganic base,
wherein:
—X$^2$ is independently —Cl, —Br, or —I; and
—R$^E$ is a carboxylic acid-protecting ester group;
or
(ii): by an alkenyl-carboxylic acid addition (ACAA-1) step comprising reacting a compound of Formula (C):

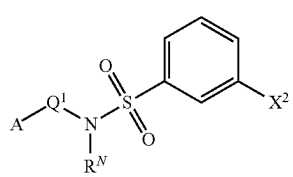
(C)

with a compound of Formula (D'):

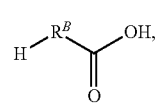
(D')

wherein:
—X$^2$ is independently —Cl, —Br, or —I;
(b) an optional purification (PUR$^F$) step comprising optionally purifying said compound of formula (F);

(c) forming a compound of formula G by a hydroxamic acid formation (HAF) step comprising:
(i) reacting said compound of Formula (F):

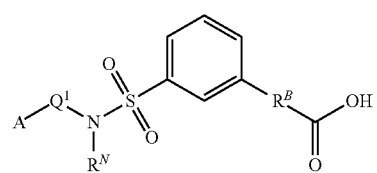
(F)

with either thionyl chloride (SOCl$_2$) or oxalyl chloride (C$_2$O$_2$Cl$_2$) to form an intermediate product (F'); and
(ii) reacting said intermediate product (F') with hydroxylamine (NH$_2$OH) to form a compound of Formula (G):

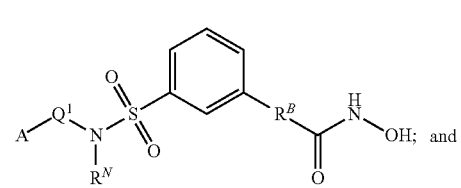
(G)

(d) an optional purification (PUR$^G$) step comprising optionally purifying said compound of formula (G).

2. The method according to claim 1,
wherein said compound of Formula (F):

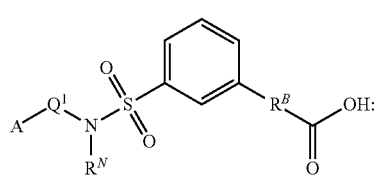
(F)

is synthesized by said alkenyl-acid addition (AAA) step (a) comprising, in order:
an alkenyl-carboxylic acid ester addition (ACAEA-1) step comprising reacting a compound of Formula (C):

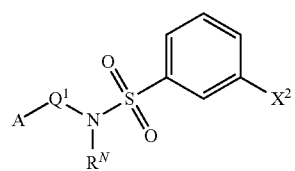
(C)

with a compound of Formula (D):

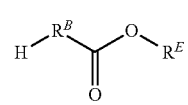
(D)

to form a compound of Formula (E):

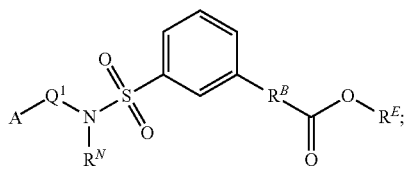
(E)

an optional purification (PUR$^E$) step comprising optionally purifying said compound of formula (E); and
reacting said compound of Formula (E) with a de-esterification agent, wherein the de-esterification agent is an acid, or an inorganic base, to form a compound of Formula (F);
wherein:
—$X^2$ is independently —Cl, —Br, or —I; and
—$R^E$ is a carboxylic acid-protecting ester group.

3. The method according to claim 1,
wherein said compound of formula (C):

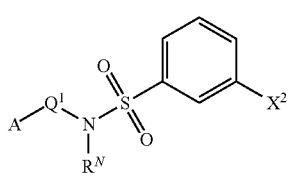
(C)

is synthesized by
a sulfonamide addition (SAF-1) step comprising
reacting a compound of Formula (A):

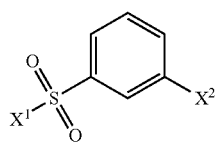
(A)

with a compound of Formula (B):

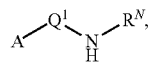
(B)

wherein:
—$X^2$ is independently —Cl, —Br, or —I; and
an optional purification (PUR$^C$) step comprising optionally purifying said compound of formula (C).

4. The method according to claim 3,
wherein said compound of Formula (F):

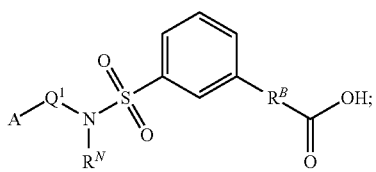
(F)

is synthesized by said alkenyl-acid addition (AAA) step (a) further comprising, in order:
an alkenyl-carboxylic acid ester addition (ACAEA-1) step comprising
reacting a compound of Formula (C):

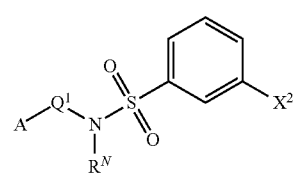
(C)

with compound of Formula (D):

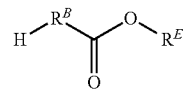
(D)

to form a compound of Formula (E):

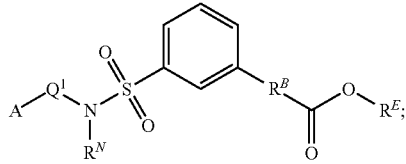
(E)

an optional purification (PUR$^E$) step comprising optionally purifying said compound of formula (E); and
a carboxylic acid deprotection (CAD-1) step comprising
reacting said compound of Formula (E):

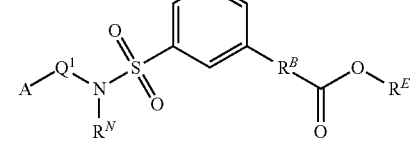
(E)

with a de-esterification agent, wherein the de-esterification agent is an acid, or an inorganic base,
wherein:
—$X^2$ is independently —Cl, —Br, or —I; and
—$R^E$ is a carboxylic acid-protecting ester group.

5. The method according to claim 1, wherein -$A^1$, if present, is independently phenyl, and is optionally substituted.

6. The method according to claim 1, wherein -$Q^1$ is independently a covalent bond.

7. The method according to claim 1, wherein —$R^N$ is independently —H or saturated aliphatic $C_{1-4}$-alkyl.

8. The method according to claim 1, wherein —$R^{B1}$, present, is independently: —CH=CH—, —CD=CH—CH$_2$—, or —CH=CH—CH=CH—.

9. The method according to claim 1, wherein:
- A is independently phenyl;
- $Q^1$- is independently a covalent bond;
- $R^N$ is independently —H or aliphatic $C_{1-4}$alkyl; and
- $R^B$— is independently —CH=CH—.

10. The method according to claim 1, wherein:
- A is independently phenyl;
- $Q^1$- is independently a covalent bond;
- $R^N$ is independently —H or -Me; and
- $R^B$— is independently —CH=CH—.

11. The method according to claim 1, wherein:
- A is independently phenyl;
- $Q^1$- is independently a covalent bond;
- $R^N$ is independently —H; and
- $R^B$— is independently —CH=CH—.

12. The method according to claim 1, for the synthesis of a compound of the following formula or a pharmaceutically acceptable salt thereof

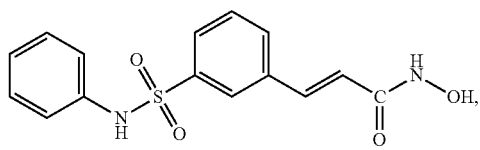
(7)

said method comprising, in order:
(A) either (i): in order:
reacting a compound of Formula (3):

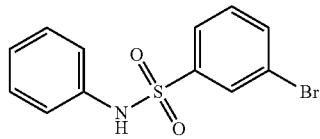
(3)

with a compound of Formula (4):

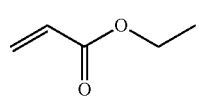
(4)

to form a compound of Formula (5):

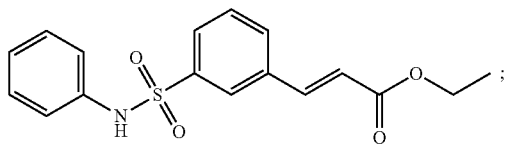
(5)

optionally purifying said compound of Formula (5); and
reacting said compound of Formula (5) with a de-esterification agent, wherein the de-esterification agent is an acid, or an inorganic base, to form a compound of Formula (6):

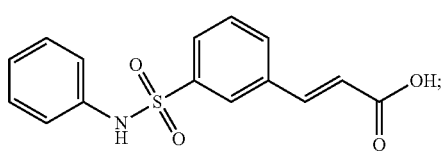
(6)

or (ii):
reacting a compound of Formula (3):

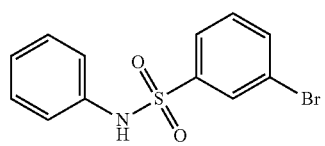
(3)

with a compound of Formula (4'):

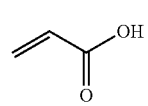
(4')

to form a compound of Formula (6):

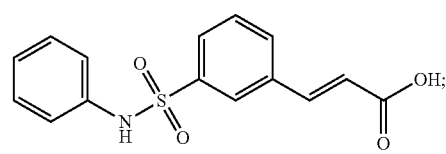
(6)

(B) optionally purifying said compound of Formula (6);
(C) reacting said compound of Formula (6) with thionyl chloride ($SOCl_2$) to form an intermediate product (6');
(D) reacting said intermediate product (6') with hydroxylamine ($NH_2OH$) to form said compound of Formula (7); and
(E) optionally purifying said compound of Formula (7).

13. The method according to claim 12, wherein said compound of Formula 6 is synthesized by step (A) comprising, in order:
reacting a compound of Formula (3):

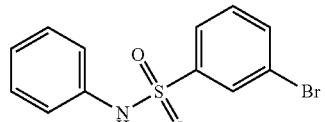
(3)

with a compound of Formula (4):

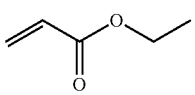
(4)

to form a compound of Formula (5):

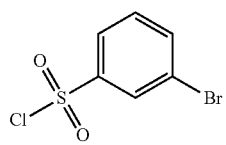

optionally purifying said compound of Formula (5); and reacting said compound of Formula (5) with a de-esterification agent, wherein the de-esterification agent is an acid, or an inorganic base, to form a compound of Formula (6):

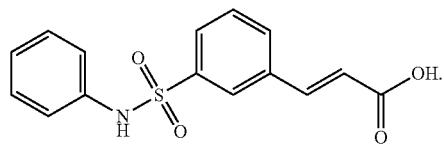

14. The method according to claim 12, wherein, said compound of formula (3) is synthesized by reacting a compound of Formula (1):

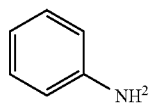

with a compound of Formula (2):

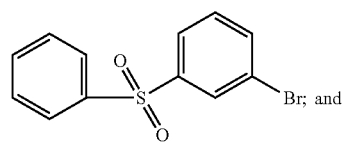

to form said compound of Formula (3):

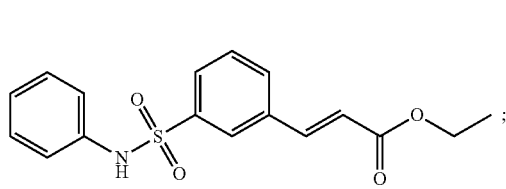

optionally purifying said compound of Formula (3).

15. The method according to claim 14, wherein said compound of Formula 6 is synthesized by step (A) comprising, in order:

reacting said compound of Formula (3):

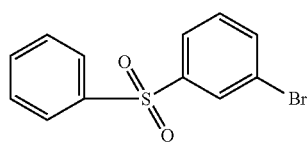

with a compound of Formula (4):

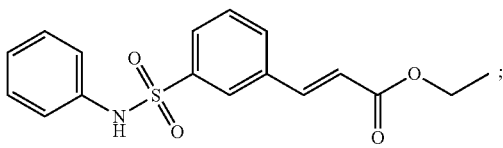

to form a compound of Formula (5):

(5)

optionally purifying said compound of Formula (5); and reacting said compound of Formula (5) with a de-esterification agent, wherein the de-esterification agent is an acid, or an inorganic base, to form a compound of Formula (6):

(6)

16. A compound of Formula (G), or a pharmaceutically acceptable salt thereof, obtained by the method of synthesis according to claim 1.

17. A compound of Formula (F), or a pharmaceutically acceptable salt thereof, obtained by a method of synthesis according to claim 1.

18. A compound of Formula (E), or a pharmaceutically acceptable salt thereof, obtained by the method of synthesis according to claim 1.

19. A compound of Formula (C), or a pharmaceutically acceptable salt thereof, obtained by the method of synthesis according to claim 3.

20. A method of treatment of a disease or disorder which is mediated by HDAC, in a patient, comprising administering to said patient a therapeutically-effective amount of a compound of Formula (G) obtained by a method of synthesis according to claim 1.

* * * * *

UNITED STATES PATENT AND TRADEMARK OFFICE
CERTIFICATE OF CORRECTION

PATENT NO. : 8,642,809 B2
APPLICATION NO. : 12/678594
DATED : February 4, 2014
INVENTOR(S) : Reisch et al.

It is certified that error appears in the above-identified patent and that said Letters Patent is hereby corrected as shown below:

In the Claims

Column 49, line 12- "formula (E); and" should read --formula (E); and a carboxylic acid deprotection (CAD-1) step comprising--.

Column 49, line 52- "$X^2$" should read --$X^1$--.

Column 50, line 66- "present, is independently:" should read --if present, is independently:--.

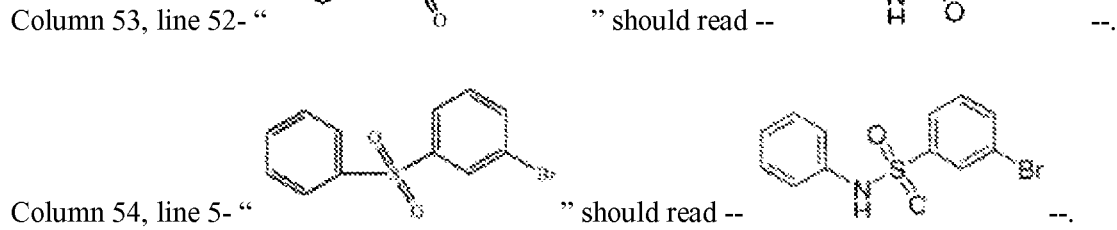

Column 53, line 52- " [structure] " should read -- [structure] --.

Column 54, line 5- " [structure] " should read -- [structure] --.

Signed and Sealed this
Tenth Day of November, 2015

Michelle K. Lee
*Director of the United States Patent and Trademark Office*